(12) United States Patent
Menczel et al.

(10) Patent No.: US 9,314,206 B2
(45) Date of Patent: Apr. 19, 2016

(54) DIET AND CALORIES MEASUREMENTS AND CONTROL

(71) Applicant: Memphis Technologies, Inc., Boca Raton, FL (US)

(72) Inventors: Yaron Menczel, Mevasseret Zion (IL); Yair Shachar, Ramat Gan (IL); Odelia Weiss, Ritzon Lezion (IL)

( * ) Notice: Subject to any disclaimer, the term of this patent is extended or adjusted under 35 U.S.C. 154(b) by 189 days.

(21) Appl. No.: 14/078,675

(22) Filed: Nov. 13, 2013

(65) Prior Publication Data

US 2015/0132722 A1     May 14, 2015

(51) Int. Cl.
| | |
|---|---|
| *G09B 19/00* | (2006.01) |
| *A61B 5/00* | (2006.01) |
| *G06F 19/00* | (2011.01) |
| *A61B 5/117* | (2006.01) |

(52) U.S. Cl.
CPC .......... *A61B 5/4866* (2013.01); *G06F 19/3475* (2013.01); *G09B 19/0092* (2013.01); *A61B 5/117* (2013.01)

(58) Field of Classification Search
USPC ........................................................ 434/127
See application file for complete search history.

(56) References Cited

U.S. PATENT DOCUMENTS

| | | |
|---|---|---|
| 6,283,914 B1 | 9/2001 | Mansfield et al. |
| 6,287,262 B1 | 9/2001 | Amano et al. |
| 6,561,415 B2 | 5/2003 | Grant |
| 7,123,956 B2 | 10/2006 | Oguma |
| 7,182,248 B2 | 2/2007 | Ookushi |
| 7,432,454 B1 | 10/2008 | Sze et al. |
| 7,914,468 B2 | 3/2011 | Shalon et al. |
| 8,122,259 B2 | 2/2012 | Menczel et al. |
| 8,299,930 B2 | 10/2012 | Schmid-Schonbein et al. |
| 8,310,368 B2 | 11/2012 | Hoover et al. |
| 8,330,057 B2 | 12/2012 | Sharawi et al. |
| 8,345,930 B2 | 1/2013 | Tamrakar et al. |
| 8,363,913 B2 | 1/2013 | Boushey et al. |
| 8,439,683 B2 | 5/2013 | Puri et al. |
| 8,504,145 B2 | 8/2013 | Kuroda et al. |
| 8,549,319 B2 | 10/2013 | Menczel et al. |
| 2001/0043968 A1 | 11/2001 | Rhee |
| 2007/0173703 A1 | 7/2007 | Lee et al. |
| 2009/0012433 A1 | 1/2009 | Fernstrom et al. |
| 2009/0192901 A1 | 7/2009 | Egeresi |
| 2009/0216755 A1 | 8/2009 | Itamar |
| 2012/0077153 A1 | 3/2012 | Livny |
| 2013/0044042 A1 | 2/2013 | Olsson et al. |
| 2013/0085345 A1 | 4/2013 | Geisner et al. |
| 2013/0152002 A1 | 6/2013 | Menczel et al. |

*Primary Examiner* — Kesha Frisby
(74) *Attorney, Agent, or Firm* — Mitchell A. Rossman; Terra Nova Patent Law, PLLC

(57) ABSTRACT

The present invention depicts systems and methods for utilizing sensors and other means that are able to track a User, and grasp his pattern of food intake (e.g., the volume, Calories, content, and other attributes of food entities), Calories outtake, and online network capabilities for tracking the balance of User Calories and other nutritional attributes.

7 Claims, 27 Drawing Sheets

Feb 13, 2013 1:54:31
Green Salad
110 Gram
French Fries
130 Gram
Diet Cola
200 Gram
Beef Steak
240 Gram
FIG. 20

DIET AND CALORIES MEASUREMENTS AND CONTROL

BACKGROUND OF THE INVENTION

People across the world have long been challenged by the need to restrain their diet and eat healthy food. Diet related issues are mostly pertain to weight watching, but also include allergies of special kind, and avoidance of specific food. Different Users with a varied set of characteristics (e.g., age, gender, ethnicity, physical attributes, health conditions, skill level, general attitude, and others) would inherently have different needs and preferences.

The common approach to deal with this problem is to apply self-discipline. A User is instructed to avoid or limit certain foods (frequently sweets and in many cases high carbohydrate foods in general, and to attempt to count manually the Calories that one consumes. A User will typically do a poor job in estimating the volume of food he is eating and to figure the amount of Calories in each particular item. However, he will be able to determine much better than any computerized algorithm what exactly he is eating, although he may be wrong in many of the cases.

Another deficiency of the aforementioned common approach is the fact that it needs constant book keeping. The User needs to register constantly the amount of food he had. Unless he uses some sort of an application to write that data, he cannot keep a track of it, and compare the results to the actual weight fluctuations. Even if he does that, it is a very tedious task.

A product called Google Glasses is being marketed by Google Inc., and also described in U.S. Patent Application Publication No. 20130044042 (by Google Inc.), can be used in embodiments of the present invention. The Google Patent Application Publication is about a frame of glasses, a camera, microphone, and an electronic device embedded inside, that among other functions can be used to conduct Blue Tooth or other wireless communication. This Patent Application Publication does not specify any useful application associated with those glasses, and in particular nothing related to Calorie Counting or Food analysis as described in the present invention.

Another product called Telepathy One is also a wearable unit that is connected to the User ear, and includes a camera, and potentially a transmitter.

A product called Tellspec uses a laser transmitter and a spectrum receiver with belief that each food type will have a unique spectrum signature.

U.S. Pat. No. 8,345,930 describes a method of estimating a volume of one food item on a food plate. This patent gives a partial solution to some of the many issues described in the present invention, but it fails to show what the food type is in the ways described by embodiments of the present invention. The above '930 patent also lacks a disclosure of methods for analyzing how much of what is on the plate that the User actually ate and many other issues described in the present invention. In addition, the method of finding volume is improved vastly by embodiments of the present invention.

U.S. Pat. Nos. 8,299,930 and 8,310,368 each describe a method of estimating a Bite size. The methods that U.S. Pat. Nos. 8,299,930 and 8,310,368 each use to estimate a Bite size may be employed for embodiments of the present invention, but it depicts considerable disadvantages. For example, the User is forced to wear external elements inside his mouth (tooth sensor) on his body and wrist (accelerometer), so a fork movement or wrist movement will be detected and from that the logic will determine that a Bite chewing is done. As opposed to that, embodiments of the present invention teach using standard hardware that will become one day in regular use, like Google Glasses.

U.S. Pat. No. 7,914,468 suggests counting Bites for the sole purpose of controlling User's appetite. That patent does not use Food Type to determine the volume or weight of each Bite.

U.S. Pat. No. 8,330,057 describes a method for using an external container with sensitive scales and a processor to calculate the number of Calories in the food item based on weight, type of food and mode of preparation.

Video Scene analysis is an active research dated from the mid 1990's. There are many techniques proposed in the literature, pertaining to how to perform Scene Analysis on a Video scenery, which includes 30 (24) frames per second. In particular, Bouthemy et al proposed a template based architecture to analyze so called shots, which are detected using MPEG I Frames.

What is needed in the art is the disclosure of new systems and methods, which will be able to track a User, and grasp what he is eating, what is the content of that food and possibly analyze food intake vis-à-vis the User Calorie balance and body weight plan.

SUMMARY OF THE INVENTION

Embodiments of the present invention depict systems and methods for utilizing sensors and other means that are able to track a User, and grasp his pattern of food intake (e.g., the volume, Calories, content, and other attributes of food entities), Calories outtake, and online network capabilities for tracking the balance of User Calories and other nutritional attributes. As an exemplary case to illustrate some aspects of the invention is a User equipped with glasses (a non-limiting example) that is viewing and listening constantly to the food intake. That food intake can be provided in multiple ways. Here are some non-limiting examples:

a. In a restaurant or home, a User gets a plate and eats some part of its content.

b. A User noshes some food from the refrigerator, from a closet, or in a setting where food is around, and he takes what he wants directly.

c. A User is invited to an outdoor setting like a Barbecue and served some food. Embodiments of the present invention also show how the food intake by the User is tracked, and the volume/weight is computed. Then, an ingredient analysis is conducted and the User is notified on deviations from plan. Embodiments of the present invention also depict systems and methods for tracking user calories expenditure, calorie balance and other related information items, as well as distributed nutrition and calorie balance control, calorie account and data sharing services. Addition aspects are disclosed herein as part of the detailed description of the invention.

The present invention is better understood upon consideration of the detailed description of embodiments disclosed herein, in conjunction with the accompanying drawings.

BRIEF DESCRIPTION OF THE DRAWINGS

Embodiments of the invention may be best understood by referring to the following description and accompanying drawings, which illustrate such embodiments. In the drawings:

FIG. 20 provides an exemplary description of the portion records the user had for lunch in an exemplary embodiment.

Figure 1:
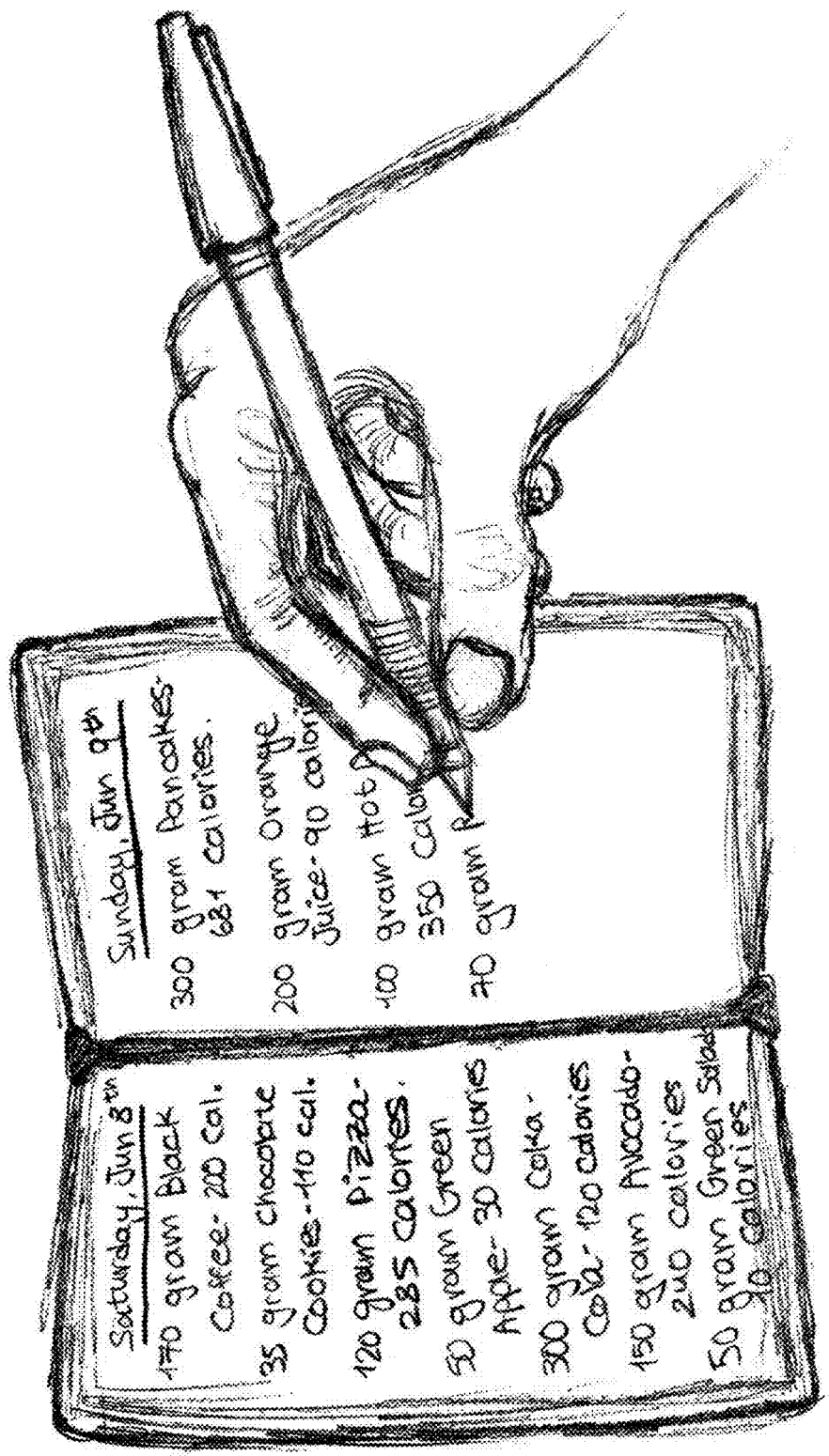
FIG. 1 is a background way of accomplishing Calorie counting.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention depicts new systems and methods for utilizing sensors and other means that are able to track a User, and grasp what he is eating, the volume/weight of each piece of food, and what is the content of that food (Calories, ingredients, protein, carbs, fats, Sodium, vitamins, etc.).

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events, which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *The American Heritage Dictionary of the English Language*, Houghton Mifflin, Boston Mass., 1981.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As used herein, the terms "one embodiment," "an embodiment" or "another embodiment," etc. mean that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the terms "include," "for example," "for example," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As a motivation to the usefulness of the system, notice the following advantages of the present invention. A common approach as described in FIG. 1 is to tell a User to write down all he eats in one day. The belief is that by doing this tedious work, the User will learn to constrain himself.

Here we describe an exemplary embodiment that performs automatically all the work for the User and in addition provides him with a constant monitoring as well as daily, weekly, and monthly reports of what he eats, in various representations. Here are some non-limiting examples:

a. By food type and volume/weight of food
b. By ingredients (Carbs, Protein, Fat, Saturated Fat, Sodium, Vitamins, minerals, etc.)
c. By raw data Calories (from protein, from fat, from saturated fat, from complex carb, from heated food, etc.)
d. By Minerals (sodium, magnesium, iron, etc.)
e. By fiber consumed
f. By Cholesterol (LDL, HDL)
g. By sugar (Glucose, Fructose)
h. By liquid consumed (water, water from food, regular coffee, decaf coffee, sodas, diet Coke, etc.)
i. Analysis of the Calories consumed using multiple theorems that take into account the type of food, the timing of eating, the length to chew and the length of the meals, water and other liquid consumed in relationship to the food consumed, User profile, interaction with other food dietary induced thermogenesis (DIT), and other parameters.
j. Full analysis that takes into account food intake as well as workout activities that reduces Calories. In addition, ambient parameters, like outside temperature and humidity, location (out of home), and others will be taken into account.

In one embodiment, a System is depicted which identifies food types and volumes/weights that the User eats in manners to be described, nutritional information items each describing at least one ingredient of the food and additional information on each such intergradient such as its weight, volume, proportion, caloric value, etc. The system may then further furnish the User with many useful indications, such as the amount and type of Vitamins and Minerals that one is eating per day. The system may build a history of what the User has been eating, which he or his health professional may analyze.

In yet another embodiment, a User will specify a set of restrictions that he would wish the system to monitor. In the simplest case, the User will ask to have at most N Calories a day (e.g., 1400 Calories). However, the set of restrictions can be much richer. Some diets allow you one free day. So, he can program the system to have 6 days of Calories restriction, and one day of a much higher bound of Calories.

The restrictions can be of many ingredients' constraints. For instance, in order to keep a balanced Diet, a User can specify that he wants to eat 30% Carbs, 40% Protein, and 30% Fat. Also, the System can give upper limits for certain ingredients such as Sodium (1500 mg). Also, the System can give a minimum limit of other ingredients that if the User is not eating, he or she will be notified (e.g., iron 10 mg a day). The system monitors the User's food intake and smartly notifies the User when he or she deviates from the plan. Obviously, on the first meal of the day, he may have a deviation. The system, will have a threshold based on Calories or weight or any other suitable parameter, that only after passing that Threshold, and only after the Deviation is far enough (e.g., 10%), and further into the day (e.g., second meal), then it notifies the User. At the end of day (as a non-limiting example), the User is notified on those ingredients that he is lacking, and those ingredients that he overtook.

Table 1 describes an example of the constraints that a User will give the System. The way the User inputs that table is implementation independent and it can be by filling a Questionnaire on an Apple iPad or a similar device, answering voice questions, and or pointing to different possibilities when asked.

TABLE 1

| Days | Monday | Tuesday | Wednesday | Thursday | Friday | Saturday | Sunday |
|---|---|---|---|---|---|---|---|
| Max calories | 1700 | 1700 | 1700 | 1700 | 1700 | 1300 | 2400 |
| | Carb | | Protein | | Fat | | Other |
| Mix | 24% | | 42% | | 31% | | 5% |
| Allergies | Peanuts | | Gluten | | Lactose | | Cashew Nuts |
| | No | | No | | No | | Most 20 grams a day |
| Illness | Diabetes Type 2 | | Gout | | Hypertension | | Acne |
| | No | | | | | | |

Another exemplary case pertains to User suffering from allergies, or having food constraints. If a User cannot eat certain ingredients (e.g., Peanuts, Gluten or Lactose) or wants to restrain the amount of certain ingredients (e.g., Cashew Nuts), this can be easily done, by specifying as an example:

1. Peanuts—no intake because of allergy
2. Cashew Nuts—20 gram a day because of Diet Another example is of a User having a non-stable Diabetes Type 2. The system will automatically is aware that he is not allowed to eat more than 100-130 gram of Carbohydrates. Fruits and Vegetables are allowed as long as he is not getting more than 10 grams of sugar.

Another non-limiting example of a common disease is Gout. The restriction there, for example, is up to 75 gram of Protein a day (800 grams per week). The System automatically calculates the number of grams of Protein consumed by the User, and provides him with the appropriate feedback.

Similarly, control of additional food attributes and/or ingredients such as Glycemic Index, Glycemic load may also be measured and controlled according this embodiment and other embodiments of the present invention.

Referring to Table 2, which can be used in an exemplary embodiment to illustrate the knowledge the System has about certain illnesses.

TABLE 2

| Illness | Ingredient | Daily max | Weekly max |
|---|---|---|---|
| Diabetes type 2 non stable | Carbohydrates | 130 grams | 900 grams |
| Diabetes type 2 non stable | Glucose | 20 mg | 140 mg |
| Gout | Protein | 75 grams | 800 grams |
| Hypertension | Sodium | 350 milligrams | 3100 milligrams |
| Acne | Fat | 600 grams | 3000 grams |

In yet another exemplary embodiment, a method for protein control for vegans is depicts. It is a well-known fact that vegans may suffer from lack of protein due to their strict diet restriction. For that purpose, a vegan should explicitly add to his diet some protein rich supplements, such as Tofu, Beans, Lentils, and Nuts. In this embodiment, an alert will be given in case the User does not have at least a given level of protein intake during a predefined period of time. In a similar way, the System may track for at least a minimal food intake (rather than maximal intake) of any other nutritional ingredient or a combination of ingredients. The System may also track for at least a minimal food intake of a given nutritional ingredients set A, while tracking for a maximal intake limit for a given nutritional ingredients set B. The set A, B can be identical, dissimilar or disjoint. The set A, B may include, for example, distinct ingredients as elements and/or combined ingredients and/or formulas describing connections between ingredients.

In yet another embodiment, there will be tracking of noshing of food. Take several examples that will be described:
 1. A User eats grapes from a cluster of grapes.
 2. A User eats ice cream directly from an Ice Cream Box.
 3. A User takes a piece of bread (or cracker) and dips it in some bawl, like humus or onion dip.
 4. A User eats several potato chips from s potato chip bag.
 5. A User eats M&M from his hand.
 6. A User eats a hamburger bun, hot dog bun, or a Pita filled with some kebab.
 7. A User eats popcorn in a movie theatre.

There are many more examples of food intake that need to be addressed and described. We will give a generic solution to one of those noshing problems that can be adapted to each class of problems (see, e.g., the Hand analysis described herein below).

There are many other usages to the data accumulated about the User's eating habits. The User can get automatic notifications on the dangers of what he is eating and what he is not eating. In another exemplary embodiment, the System is designed to alert the User if the foods he is eating can be a hazard to his health (e.g., allergens), and the specific diseases that can arise will be shown to the User. In addition, or alternatively, sponsored advertising will be displayed to a User who complies with certain attributes (for instance, as non-limiting example, eats too much Sodium per day, or is missing Magnesium minimum level).

In another exemplary embodiment, a User can do a What if analysis. When the User is debating between two kind (or more) of food, the User, can then input to the System (in methods described below-either by showing the system the products or by explicitly specifying it) the different possibilities, and the System automatically tells him the ingredients in each possibility, and the ramifications to the User's diet.

Summary of Methods

In general, there are three ways that a Calorie counting (or any other food ingredient detecting method) is performed:
 a. Manual
 b. Semi-automatic
 c. Fully automatic In the Manual method, the User tells the system in possible multiple ways what he is eating, and the system makes the right calculations. In other words, the User specifies that he is eating a beef steak and in many cases its size if the User is aware of the size. The User may not tell the system in most cases, how big the steak, and how many Calories are there. The System figures the size of the steak, and the number of Calories in that steak, and more important notices, how much of the steak is consumed.

In the Semi-Automatic method, the User is asked in certain cases, what he is eating. In many cases, there is no need to do that, and the System automatically figures it. The System gives a vocal feedback of what it thinks, and the User is able to modify it, if the System is wrong.

In the Fully Automatic method, the System tracks the User's activities, and makes decisions on what he is eating, totally independently. A feedback is given to the User (although the User can mute it), and only in very rare cases, the User can overwrite what the System thinks he is eating.

In order to accomplish this goal, even in the simple case of the Manual method, many techniques are needed. Several non-limiting examples include:
 a. Scene analysis in the context of food. For instance, even that we know the plate has a beef steak; we need to figure the steak size (volume/weight measuring).
 b. Voice tracking that may be used in volume analysis as will be described below.
 c. Voice recognition in the context of food. A transcription of the voice is needed. Using that transcription, an analysis of the text for clues will be conducted. For instance, a User in a restaurant ordering a Diet Coke indicates that the drink he will have, is indeed a Diet Coke.

Feedback

The system monitors the food intake and gives a feedback in several ways such as Voice Message, Video Screen, Beeps, and Vibrations. The purpose of the feedback is multiple-fold:
 1. Indicates to the User what the System deduces that the User is eating.
 2. Telling the User when he deviating from his plan or he is in danger to eat something he is not allowed.
 3. Gives the User a daily or some other frequency report.

The strength of the Feedback depends on the restriction. If a User specifies that a restriction is because of a specific allergy, and if the system suspects a particular food contains the violating ingredient, the feedback will be much stronger, and only can be shut down by the User. If, on other hand, the deviation is caused by, for example, the amount of Protein that the User is eating for the day, the feedback may be much weaker and shuts itself immediately.

The system will use several methods of feedback that will show its understanding. Several non-limiting examples include:
 1. Short beep-Users are familiar with the beep that is used for scanning machines, especially in self-checking booths in supermarkets. A beep will indicate to the User that the system recognized what he ate.
 2. Long (annoying) beep-Users are familiar with long frequency changing beeps that are a becoming popular in cars to indicate closeness to other objects.
 3. Vibration—A polite way to announce the User that he is in some kind of deviation.
 4. Audio—The system will whisper to the User the Portion records.
 5. Display—The User will see using the glasses, what the system thinks he is eating. The display can also give volume and weight, and the ingredients (i.e., Calories per 100 gram, fat per 100 gram, etc.). Note that some of beeps may continue until the User explicitly shuts them down.

User's Input

In the Manual (Training) and Semi-Automatic mode, the User is able to indicate to the system what is the food type, food name and volume/weight. The User is also able to click on the appropriate Video frame that the system will associate with the Portion record. In case, the system is either wrong or confused there are several ways to fix it: Several non-limiting examples include:

1. Voice—The User whispers to the system the Type of Food and approximate volume/weight.

2. Selection from a menu—The User gets a menu displayed on his glasses, and picks one of the items by applying on some sliding device (rolling his eyes, touching a roller, or similar). There may be multiple menus, to limit the number of items per menu.

3. Typing—The User uses a device (such as a smart phone) to type the food type, food name and volume/weight.

DEFINITIONS

The basic unit that we use in embodiments of this invention is designated as a Bite. That is the piece of food entered at one time to the User mouth. Embodiments of the present invention provides means for consumption analysis by calculating what the person takes into his mouth, and not what he has been served, as there can be a discrepancy between those two items. More than that, the eating process is done in steps. Assume that the User has a 300 gram beef steak on his plate, and he is eating it piece by piece (that are called Bites). The accumulation of Bites will be the meal that the User has consumed. Therefore, a meal is a list of Bites. A Bite may include, for example, several types of food. An atomic Bite has only one food type. So a Bite may include multiple atomic Bites. A Portion is the name and amount of a specific food type consumed in a meal. Therefore, a meal is also a list of Portions.

Here is a brief description of the definitions used in the present invention.

1. Food name—A unique name of a specific food (e.g., Sirloin beef steak, or Cantaloupe Melon). This will be a field friendly to the User. However, the system will use Food Type for all computations. There will be an extensive table that maps every possible food name to a specific food type.

2. Food Type—A specific class of food, such as peach, beef steak, Diet Coke, etc. that the System can identify.

3. Volume/Weight—The System interchanges Volume with Weight based on Food type. User (or other tracking data such as restaurant's menu) may provide any of those fields and the system will calculate the other.

4. Plate—a description of what is in the plate at any time.

5. Hand—a description of what is in the User's hand at any time.

6. Food bag—An example of food carrying option that is not a Plate or a Hand (e.g., potato chip bag)

7. Bite—a piece of food intake by the User that enters the mouth. A Bite may include, for example, multiple food types.

8. Atomic Bite—a piece of food intake by the User that includes only one food type.

9. Portion—a list of atomic Bites of one meal sharing the same food type.

10. Meal—a list of all Bites and alternatively all Food portions.

11. P frame—a frame that can be predicted by a previous frame (from Video Compression technology).

12. I frame—a frame that cannot be predicted (not effective cost wise in bit) by a previous frame.

13. Plate portion—A Portion recorded that is found on a plate.

14. Hand portion—A Portion recorded that is found in a hand.

15. Food portion—The actual Portion consumed by the User in a meal.

16. Video clip—A clip that consists of many frames.

17. Audio clip—a soundtrack.

18. Transcript—the translation of the audio clip to text.

19. Scenery—A video clip, audio clip, transcript, and meal.

Table 3 is an example of some of the actual fields in an atomic Bite data record and also in Portion data record.

TABLE 3

|  | Type | Length |
| --- | --- | --- |
| Date/time | Date/time | 8 |
| Type Food | From a set | 8 |
| Food name | String | Variable |
| Food location type | From a set {restaurant, home, etc.} | 4 |
| Food location | From a set (actual location) | 8 |
| Volume | float | 8 |
| Weight | float | 8 |
| Time length of chewing | Integer | 4 |

Table 4 is an exemplary table that describes the nutrition contents of every food type.

TABLE 4

| | Ingredients per 100 Gram | | | | | | | | | | |
| --- | --- | --- | --- | --- | --- | --- | --- | --- | --- | --- | --- |
| Item | Calories | Calories from fat | Water | Protein | Carb | Fat | Saturated Fat | Cholesterol | Sodium | Potassium | Fiber | Iron |
| Pastrami | 146 | 53.57 | 73.6 | 21.8 | 1 | 3.57 | 3.21 | 59.88 | 2201 | 18 | 1.4 | 3 |
| Egg Salad | 318 | 272.5 | 58.56 | 9.19 | 2 | 30.25 | 5.76 | 310 | 362 | 99 | 1.2 | 5 |
| Banana | 89 | 0 | 65.12 | 1 | 22.88 | 0 | 0 | 0 | 1 | 400 | 2.8 | 2 |
| Apple | 52 | 0 | 85.5 | 0.3 | 14 | 0.2 | 0 | 0 | 1 | 107 | 2.4 | 2 |

Table 5 is an exemplary description of the food Portion data record in an exemplary embodiment. Notice that is includes the date/time of when it was created, and the actual volume and weight that were consumed. As will be discussed herein below, in practice, the system records several Atomic Bite rows and aggregates them all into one food portion that contains the entire meal per food type. The main difference between a Food Portion record and the corresponding Bite records that the Food Portion record also includes the length of time for that meal, while the Bite record includes only the length of time chewing.

TABLE 5

| Date Time | Food location | Food Type | Food Name | Volume Served | Weight Served | Volume Consumed | Weight Consumed | Time |
|---|---|---|---|---|---|---|---|---|
| Jul. 14, 2013 08:12 | N.Y. Manhattan | omelet | omelet | 270 CC | 290 gr | 260 CC | 281 gr | 422 s |

Table 6 is an exemplary table that describes ambient conditions per time of day per location.

TABLE 6

Ambient conditions in a specific day using local time

| Location | 8:00 | 9:00 | 10:00 | 11:00 | 12:00 | 13:00 | 14:00 | 15:00 |
|---|---|---|---|---|---|---|---|---|
| NYC, NY USA | <12, 45> | <13, 47> | <14, 45> | <14, 50> | <16, 54> | <18, 62> | <19, 67> | <20, 72> |
| Seattle WA USA | <7, 55> | <8, 57> | <8, 58> | <9, 59> | <10, 54> | <12, 62> | <13, 67> | <12, 58> |
| Paris France | <11, 35> | <12, 57> | <13, 54> | <14, 59> | <14, 57> | <15, 62> | <14, 63> | <14, 59> |

Where <a,b> is the temperature in Celsius, and Humidity in Percentage

Heuristics

As the problem of identifying the exact food types in the meal is very hard, embodiments of the present invention may use several levels of Heuristics that help the System to identify the food types on the Plate (or in the Hand). Several non-limiting examples include:

1. Time of day/Day of Week/Day of Year-Breakfast food is different than lunch, which is different than dinner. For instance, it makes more sense that the User is eating Eggs for breakfast than for lunch. Similarly, it makes more sense that he eats Hamburger in lunch as opposed to breakfast. Food over the weekend is quite different than food over the weekdays. Therefore, data related to meals need to be attached to the day of week in order to get a better understanding of what is there. Special holidays imply different type of food and different amount consumed, for example, Thanksgiving Day meal in the United States may include turkey; Jewish Seder night i may include Matzo ball soup and no bread, and Christmas night dinner may include Marshmallow pie.

2. Training-Most Users are very conservative. They have routines, and they eat similar food in general. A System can be trained, in Manual or Semi-automatic mode, to be able to deduce later on, from similar patterns (and images), what the User is eating, based on past training.

3. Questionnaire—The System can use a Questionnaire that is given to the User such as the one in Table 7.

TABLE 7

| Question | Answer |
|---|---|
| 1. What is your favorite dessert? | A. I normally avoid dessert.<br>B. Cakes<br>C. Cookies<br>D. Fruit<br>E. Ice cream.<br>F. I don't have a preference. |
| 2. What would you rather eat? | A. Pasta<br>B. Bread<br>C. Rice<br>D. Potatoes<br>E. I don't have a preference.<br>F. None of the above. |

TABLE 7-continued

| Question | Answer |
|---|---|
| 3. What do you normally eat for breakfast? | A. I don't eat breakfast<br>B. I only drink coffee/tea.<br>C. Omelets<br>D. Cereal<br>E. Toast<br>F. Pancakes/Waffles |
| 4. Do you prefer diet drinks or regular drinks'? | A. Always diet<br>B. Diet, when possible<br>C. Cannot stand diet<br>D. Only water |
| 5. How many times a day do you normally eat snacks? | A. I don't eat snacks<br>B. 1-2 times a day<br>C. 3-4 times a day<br>D. 5 or above |
| 6. What do you prefer as a snack? | A. I don't eat snacks<br>B. Anything available<br>C. Fruit<br>D. Cookies<br>E. Chips/Pretzels<br>F. Chocolate |
| 7. How many times a day do you eat? | A. Barely once<br>B. Less than 3 meals a day<br>C. 3 meals a day<br>D. 4 meals and above<br>E. 3 meals and a few snacks<br>F. Less than 3 meals with a few snacks |
| 8. Are you: | A. Vegetarian<br>B. Vegan<br>C. None of the above |
| 9. What type of food would you rather eat? | A. Dairy<br>B. Meat<br>C. Vegetable |
| 10. What type of food would you rather eat? | A. Chinese food<br>B. Italian food<br>C. Fast food<br>D. Japanese food<br>E. None of the above |
| 11. What type of food would you rather eat? | A. Salty<br>B. Sweet<br>C. Spicy<br>D. Sour<br>E. I don't have any preference |
| 12. What type of food would you rather eat? | A. Lettuce salad<br>B. Chopped Salad<br>C. I don't have any preference<br>D. I don't eat salad. |

The Questionnaire finds out what the User eats normally, what he likes, what his cravings are, and what he cannot stand.

Based on that knowledge, the system is able to determine, that if the User does not like Broccoli, the piece of green food on his plate is not Broccoli, but maybe Lettuce.

4. Uploading of known meals—Diet companies may sponsor this kind of new technology, and will supply the system known images of plates and products that that they supply. In addition, those plates and products may be attached to barcodes and RFID repeaters that the System is able to read and analyze what is there. When it comes to do plate analysis, those downloaded images will be matched against the current plate to find similar food types, and if they have barcodes or RFID tags then the system can scan the barcode and/or read the RF data and use it to identify the food type and the volume/weight served.

5. System supplied pictures of all possible food dishes—the System will come with a generic library of all possible food types, taken in a variety of camera angles and shapes. Those downloaded pictures will be used to conduct the comparison between food items that are on the plate or in User's hand and the downloaded pictures as will be described later in the present invention.

6. Tracking Sceneries—Video and Audio clips and their associated transcriptions that are detected before food intake Sceneries. Those Tracking Sceneries contain useful information that assists in the understanding of the content of food types that the User consumes.

7. Ambient conditions—In an exemplary embodiment, all ambient parameters are recorded per a specific location, mainly temperature and humidity. The calculation on Calorie consumption may depend on the amount of liquid consumed by the User (including standard food that contain water as their largest portion), and the ambient parameters that exist at the time in the location as described below.

8. User's input—The User has the last word on what he eats. Notice that Humans may know what they are eating, but they are very weak in determining the volume and weight of each portion that they consumed. Also, their knowledge about the ingredients and in particular the number of Calories in each portion is far from being correct. Therefore, the System uses the User's input for the food name, and takes with a salt of grain the User's estimation of volume/weight. As for ingredients and Calories, the System uses that data only in extreme cases, where the User insists to overwrite the System database.

Training

Figure 2:
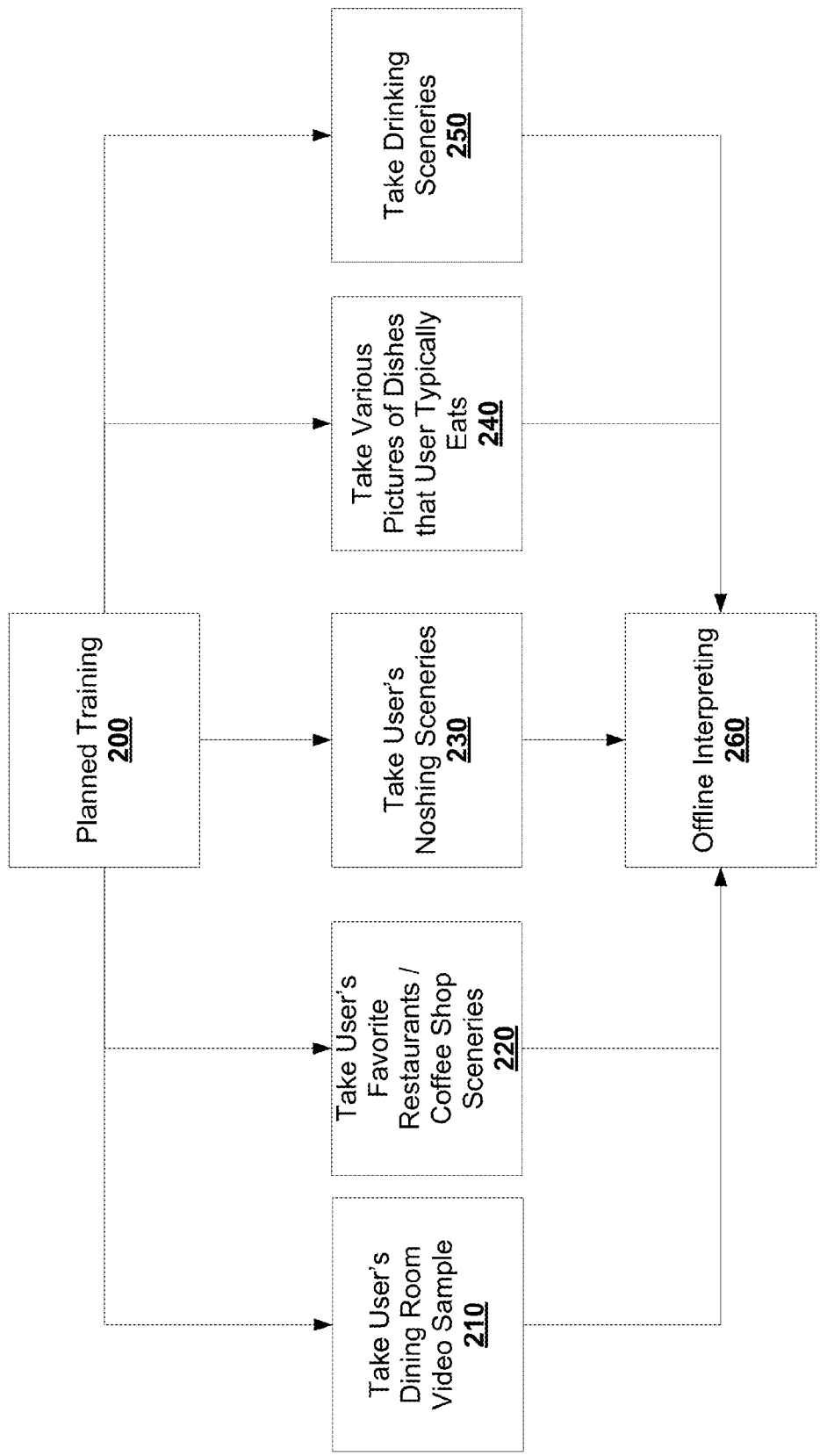
FIG. 2 is an exemplary flowchart of the planned training in an exemplary embodiment.

FIG. 2 describes an exemplary embodiment of the planned training 200. In step 210, a standard meal from the User's dining room is taken. The time of day is recorded, and based on it is determined if it is breakfast, lunch or dinner as described in FIG. 3. In Step 220, a series of training Sceneries are taken from the User's favorite restaurants and coffee shops. In step 230, the User will train with his favorite noshing (like eating a piece of fruit, eating Ice Cream, eating some cookies, etc.). In step 240, the User takes various pictures of dishes that he typically eats. In step 250, the User takes some drinking Sceneries (cup of coffee, diet Coke, water, etc.). Note, the training mode is the same as the manual mode, and the User can switch to it at any point, to improve the performance of the system in identification of food types. In step 260 there will be offline interpreting.

Figure 3:
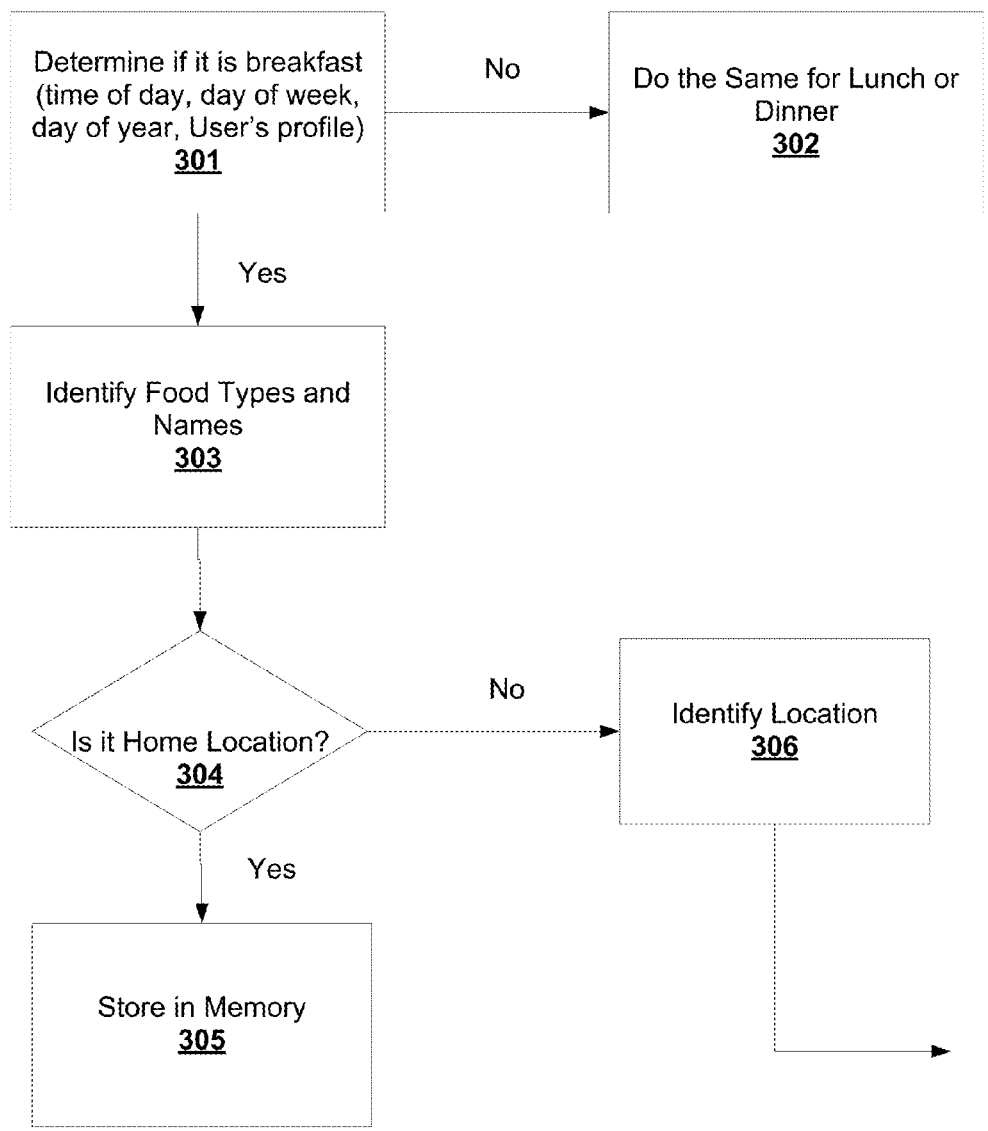
FIG. 3 is an exemplary flowchart of the daily breakfast training in an exemplary embodiment.
Figure 3:
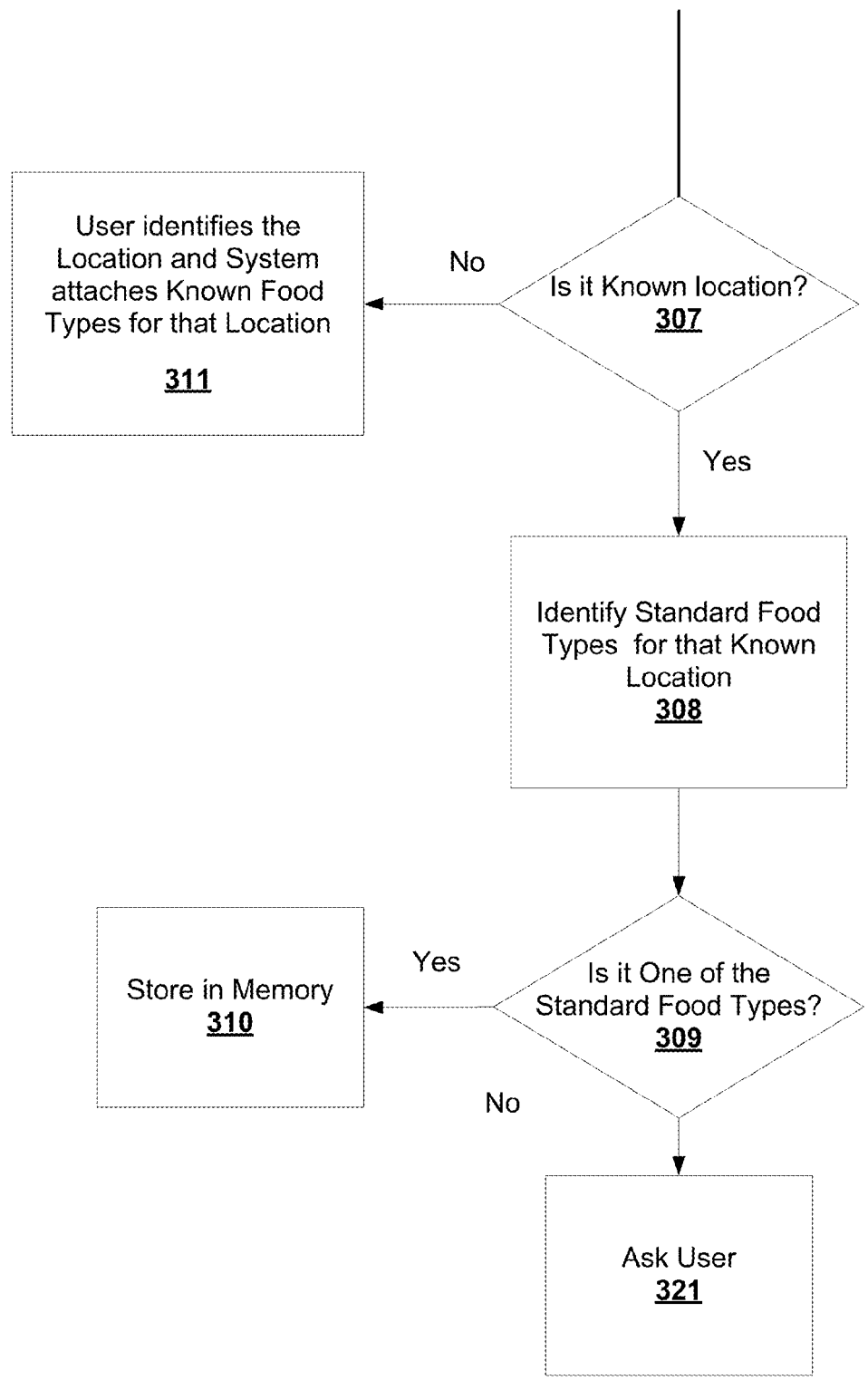

FIG. 3 describes exemplary embodiment of the daily training in the context of a breakfast setting. Step 301 checks the time of day and User's profile to determine that the context is indeed Breakfast. If that is not the case, in step 302, a similar check is done if it is a lunch or dinner setting. In step 303, the User identifies the food type and names. In Step 304, a check is made if it is home location. If so, the Frame as well as the associated food types and names are stored in memory (step 305). If not, in step 306 the User identifies the foreign location. In Step 307, it is checked if it is a known location. In Step 311, if it is not a known location the User identifies the location and the System attaches the known food types to this location. In step 308, all standard food types for that known location are retrieved. In step 309, the System determines if the food types are the same as offered in that location. If so, in step 310, that frame is stored in memory with the location and food types. Otherwise, in step 321, the User identifies new food types for that location, and they are stored in Memory with the respective frame.

Figure 4:
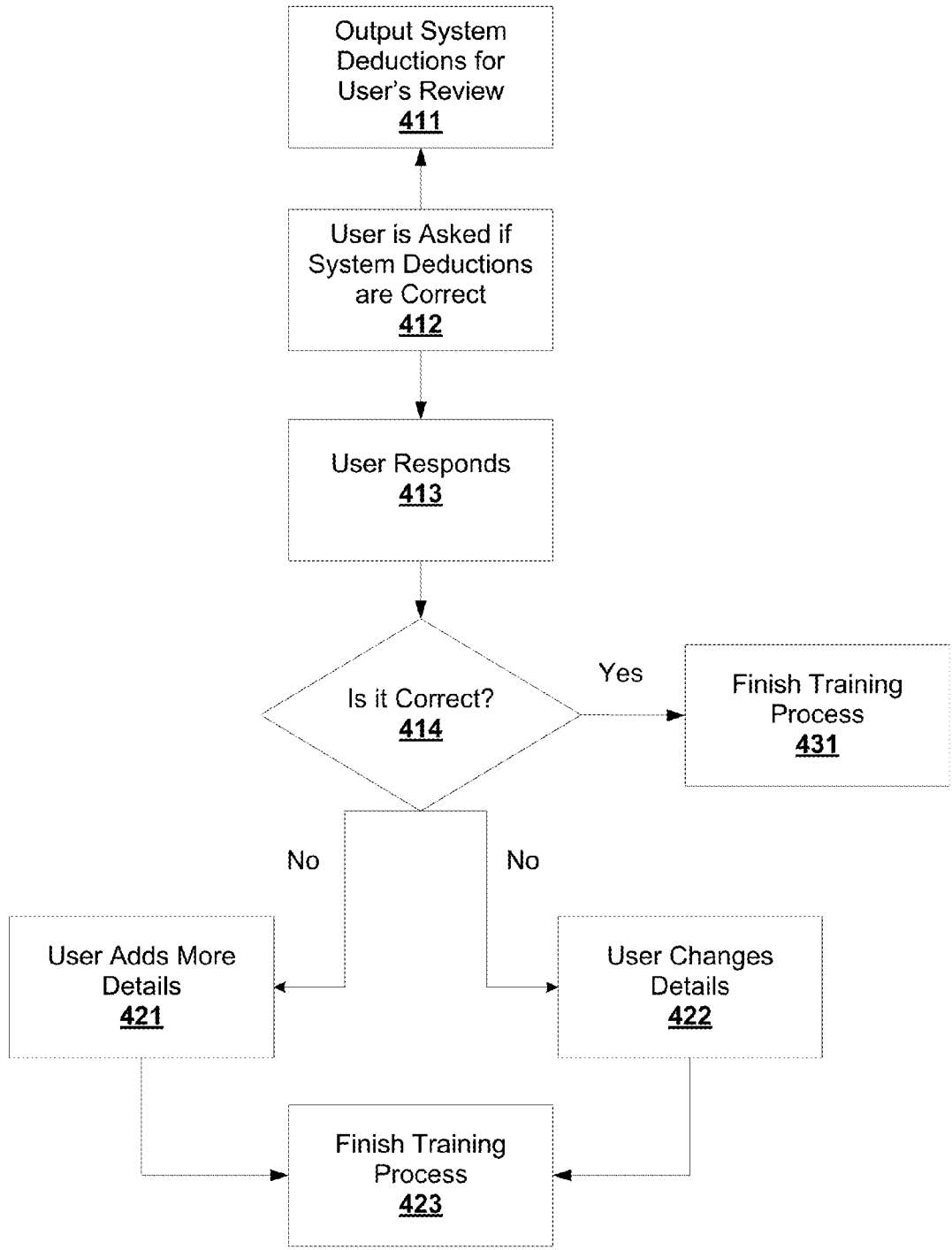
FIG. 4 is an exemplary flowchart of the offline processing of the training sceneries in an exemplary embodiment.

FIG. 4 describes the offline processing of the training sceneries in an exemplary embodiment. In step 411, the System outputs its deductions (i.e., Each portion record is associated with a single frame from the Scenery describing per that frame the food type, food name, volume and weight (both served and consumed) as described in Table 3) for User's review. The User is asked in step 412 whether the deductions are correct. In step 413, the User responds. If in step 414 it is determined that the User replied that those deductions are correct, the training process exits (step 431) and the Frame and respective Portions are stored in memory. Otherwise, in Step 421 User adds more details (like a new food type and name), and/or in step 422 the User modifies details. After finishing that iteration, the training process exits and the Frame and respective Portions are stored in Memory (step 423).

Scenery Analysis

The set of frames and associated audio clips and the deciphered transcripts that the system selected as representing what the User eats in a certain time is called a Scenery. The system differentiates between two kinds of Sceneries 1. Tracking Scenery
2. Food intake Scenery The tracking Scenery describes the process that leads to the food intake. The actual food intake Scenery describes the process of the actual food intake.

Embodiments of the present invention may first need to determine that a given Scenery is a food intake Scenery. We define food intake as the actual process of entering some food into the User's mouth.

Although it is not easy to compute directly from camera snapshots, voice analysis or physiological analysis what exactly entered the User's mouth, we will show in the next sections, that the problem is solvable in an indirect way. However, the first step is to actually detect that some food went into the User's mouth.

The entire process uses a state machine. Some of the states that we will describe are:

1. Food intake—The User is actually chewing a piece of food.
2. Food in process—the User is in the process of eating, but not necessarily is chewing at that point.

In general, in one embodiment, the system detects when the User starts eating and set the state "food in process". Then, as the system detects that the User is chewing some food the state is set to "food intake". When the User finishes chewing, the state "food intake" is reset. When there is a long pause and no detection of food intake occurs, the "food in process" state is reset.

Figure 5:
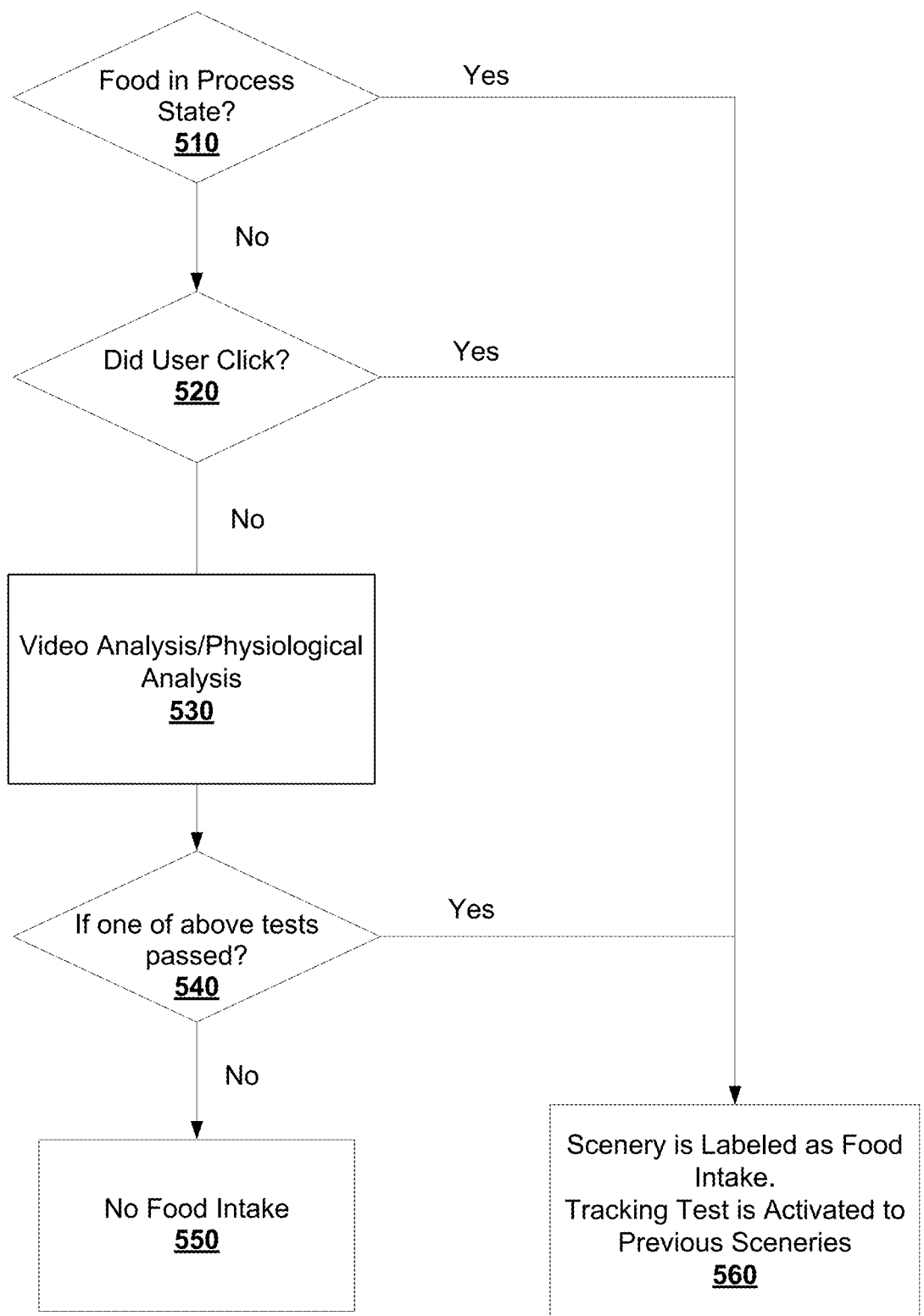
FIG. 5 is an exemplary flowchart to determine if a Scenery is a food intake Scenery in an exemplary embodiment.

FIG. 5 describes an embodiment that shows how that can be achieved. In general, there are three main methods of doing that:

1. User's report.
2. Video and Audio analysis that detect an actual food entering the User mouth.

3. Physiological analysis that detects changes in the User physiological parameters (raise of body temperature, higher blood pressure).

In Step 510, the process checks that it is not already in "food in process" state. If not, we check in step 520 if the user clicked. Especially in training, the System is allowing the User to help the System determine if there is food intake. If not, in step 530 the System performs a video analysis of the camera shots that points to the mouth to check if it can detect food intake. This is actually done based on the observation that a hand or utensil is bringing the food to the mouth (as opposed to talking where the mouth moves, but no food is entered). In step 530, the System optionally checks physiological elements such as rising of body temperature and/or raising blood pressure to try to deduce if there is food intake. If one of those tests passes (step 540), the System labels that scenery in step 560 as food intake, and set the states to "food intake" and "food in process". Otherwise, the System determines in step 550 that there is no food intake.

The two states "food intake" and "food in process" decay after a while. The "food intake" state is reset once the System detects that the chewing stops. The System uses a model of Human eating, that assumes how long it takes to chew (specific food type by a specific User), and in one embodiment, only after that period passes, the System checks Video frames and Audio Frequency patterns if the mouth is active or not (chewing food, not talking).

The "food in process" state decays after the entire meal. Once the state is set to "food in process", a process called Tracking test described below is activated to identify all the previous tracking Sceneries.

Frame Extraction from a Food Intake Scenery

The process described above that detects a food intake Scenery also labels multiple frames that describe the food intake. There are multiple types of frames. Several non-limiting examples include:
1. Plate frames
2. Hand frames
3. Bun frames (anything in a bun or Pita or Sandwich)
4. Bag frames (e.g. potato chip bag)

For each such type of frame, a corresponding analysis process is being made which is adapted to the specific frame type. For example, Bun frame analysis has different attributes compared to Plate frame analysis, since e.g. the bun as opposed to the plate, might be consumed by the user, and usually contains different food types.

The Plate frames describe the food on the plate. Each time a change in the plate is detected, a new Plate frame is created. In general, Plates are filled with food, and then the food is consumed, but this process can repeat itself multiple times during the "food in process" state.

The System creates from the Plate frames Plate Portion records. Those records don't directly show the actual food intake. However, they indicate to the System what is the actual food the User is about to eat. All the Plate Portions on the plate as well as their volumes are extracted by the Plate Analyzer (see below) and stored in consecutive Plate Portion records.

Figure 6:
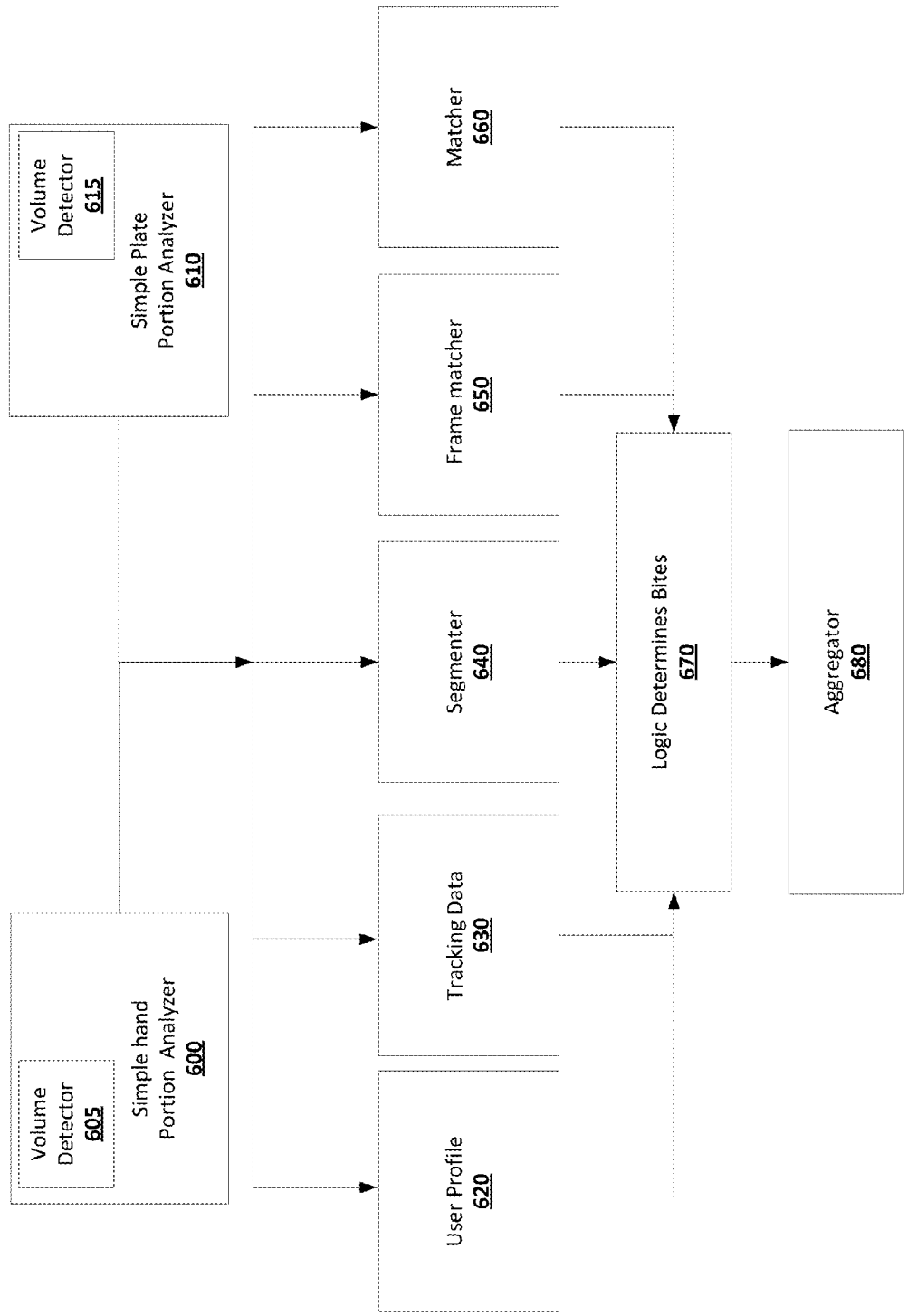
FIG. 6 is a schematic block diagram of an exemplary Meal Analysis module.

FIG. 6 is a schematic block diagram of an exemplary Meal Analysis module. It includes multiple components that are described pertaining to embodiments of the present invention to determine the type and name of each good portion that the User consumes as well to identify the volume/weight of each food item. We are describing two sub-modules:
1. Sub-module 600-simple Hand Portion Analyzer and it corresponding Volume detector (sub-module 605).
2. Sub-module 610-simple Plate Portion Analyzer and its corresponding Volume detector (sub-module 615).

Each sub-module has a Volume detector that analyzes the volume/weight of the Bites that are consumed by the User. Both sub-modules use the following generic sub-modules:
1. User profile manager—620
2. Tracking Data manager—630
3. Segmenter—640
4. Frame matcher—650
5. Matcher—660

The data generated are Bites records generated by the Bites Logic sub-module 670, and the Aggregator sub-module 680 takes those Bites and turns them to Portion records.

Figure 7:
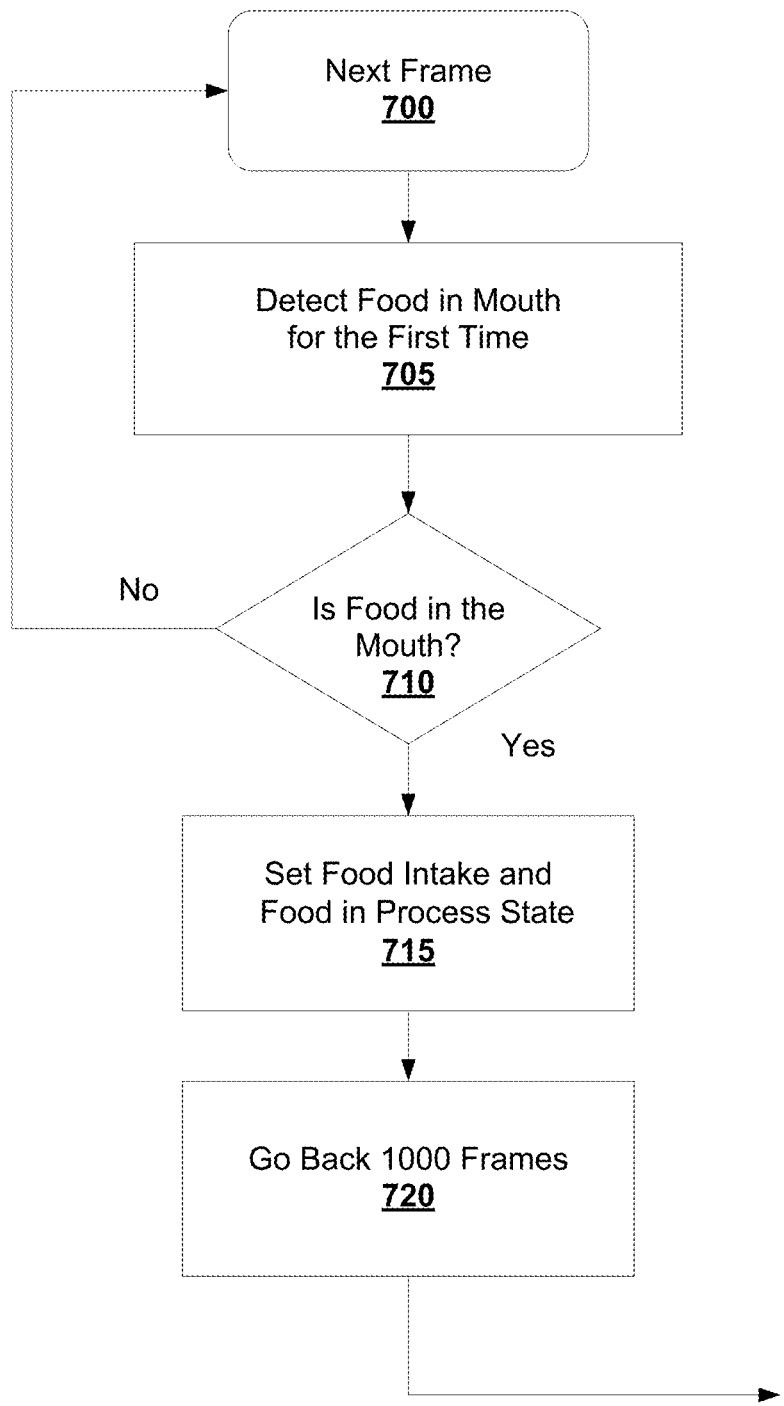
FIG. 7 is an exemplary flowchart on the operation of creating food intake images (clicks) from a scenery in an exemplary embodiment.
Figure 7:
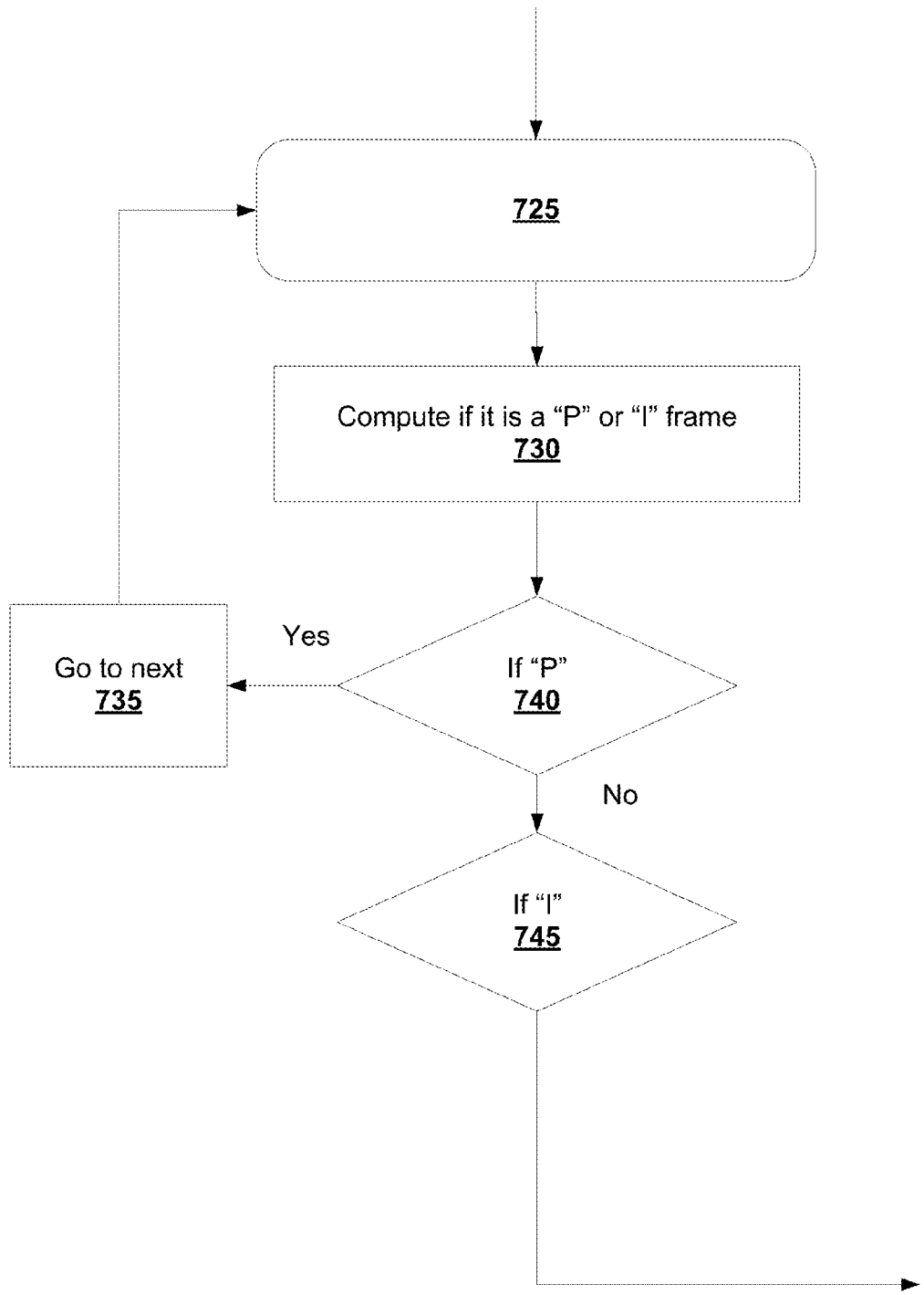
Figure 7:
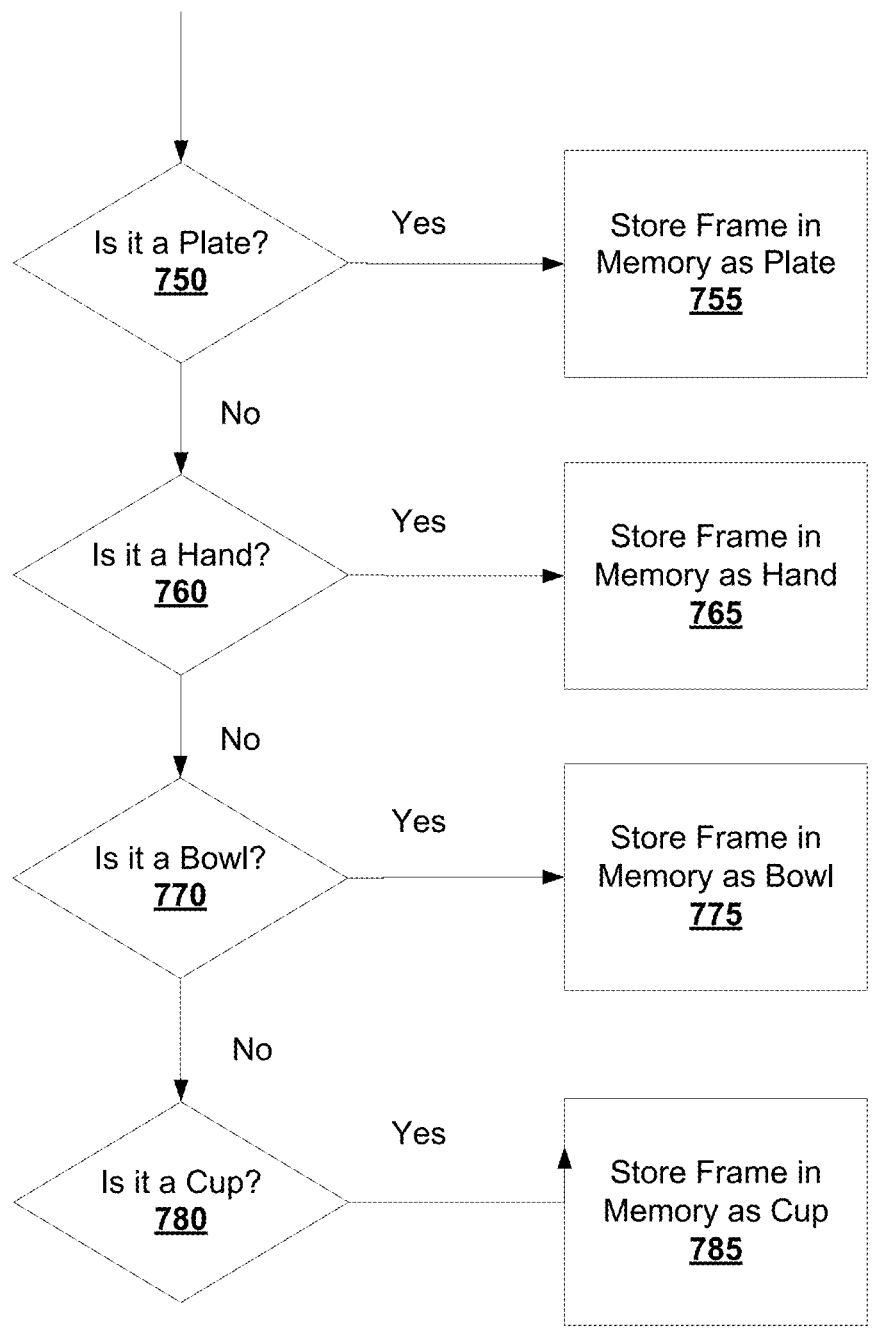

Embodiments of the present invention use Video analysis and Audio analysis for many procedures. The Video analysis processing is done using a camera and FIG. 7 shows a flowchart of doing the actual analysis. In steps 700-710 a loop inspection of frame by frame to detect food intake to the mouth for the first time (See FIG. 5 for a detailed description). In Step 715, the food intake and food in process states are set. In steps 720 to 745, 1000 frames (1000 an exemplary number, any reasonable number can work) are inspected from recent to past. Each frame is computed to check if it is a P or I frame, as typically it is done in Video Compression algorithms. Only I frames are inspected. In step 750 to step 790 various patterns are checked for each I frame. If the specific pattern is detected the loop ends in steps 755, 765, 775, 785, respectively, and that frame is stored in memory, and the right pattern state (like Plate, Hand, Bowl, Cup) is stored in memory. All the checks are exemplary ones. Real system may have hundreds of different patterns to check.

We now pay attention to two pattern states: Plate and Hand. As there are hundreds of pattern states, their treatment will follow similar concepts, but with their own pattern characteristics.

Plate Analysis

Plate Analysis is the process of analyzing in the most simplistic way what is on the plate.

Simple Plate Analysis

The Simple Plate analysis has two parts:
1. Identifying the type and name of food on the Plate
2. Identify the volume/weight of each food item The simple food type identifying is based on conventional image processing methods, used in the context of food.

Figure 8:
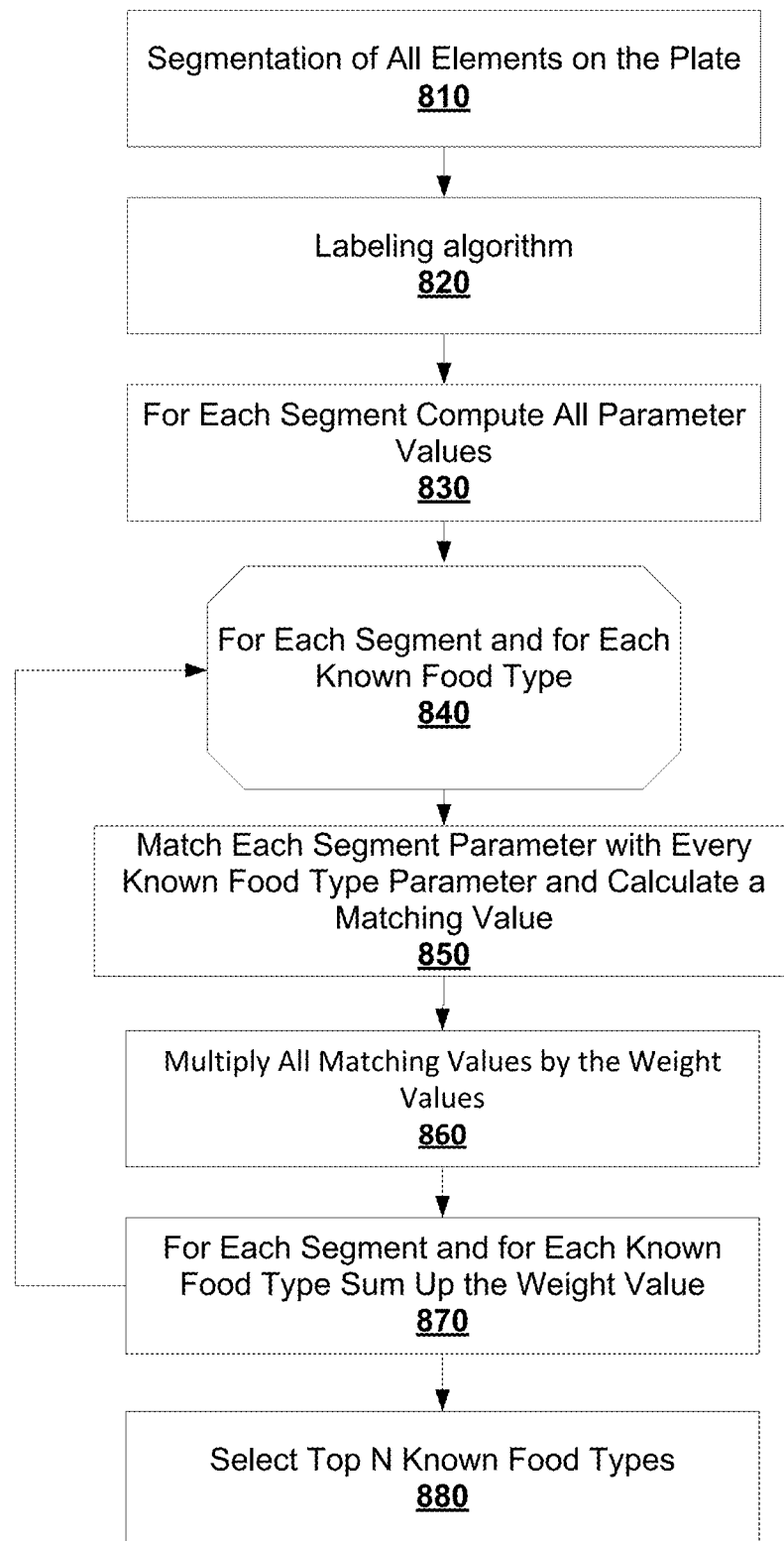
FIG. 8 is an exemplary flowchart on the operation of identifying food portions in an exemplary embodiment.

We now assume the found pattern state was a Plate. FIG. 8 describes a method, used in one embodiment, for detecting the visual features of food item that resides on the Plate at any stage (before the start of the food in process, during, and also after). In order to recognize the type of food, the System uses a table (see an example in Table 8) describing the characteristics of each food type. For instance, take beef steak as a case study, and refer to Table 8 as an exemplary embodiment.

TABLE 8

Characteristics of Beef Stake

| Parameter | From | To | Weight |
|---|---|---|---|
| Color | Brown | Black | 30% |
| Thickness | Medium | Wide | 10% |
| Texture | Coarse | Course+ | 20% |
| Shape | Circular | Elongated | 15% |
| Sizzling | Medium | High | 25% |

Referring to FIG. 8, in step 810, a standard image processing segmentation is done on the food items in the image. In step 820, the labeling algorithm merges several segments to create 3-7 segments in the plate itself. In step 830, all parameter values are computed. In step 840, a double loop is created for all segments and for all known food types. In step 850 of the double loop, we match each segment parameter with every known food type parameter and calculate a matching value. In step 860, we multiply per segment per known Food Type all matching values with the known food type parameter weight. In step 870, we sum for every segment and for every known food type the list of calculated weights. After finishing the double loop, we pick in step 880 for each segment the top N known food types with the highest calculated summary weight.

It should be noted that an Analysis (e.g., type of food) may be based not only on sensor data or heuristic knowledge but also on information explicitly provided by the User. Referring to the above example, type of food can be provided directly by the User and thus the type of food would be based on a combination of sensor and non-sensor originated information. Similarly, other Analysis can be based on any combination of sensor and non-sensor originated information.

Figure 9:
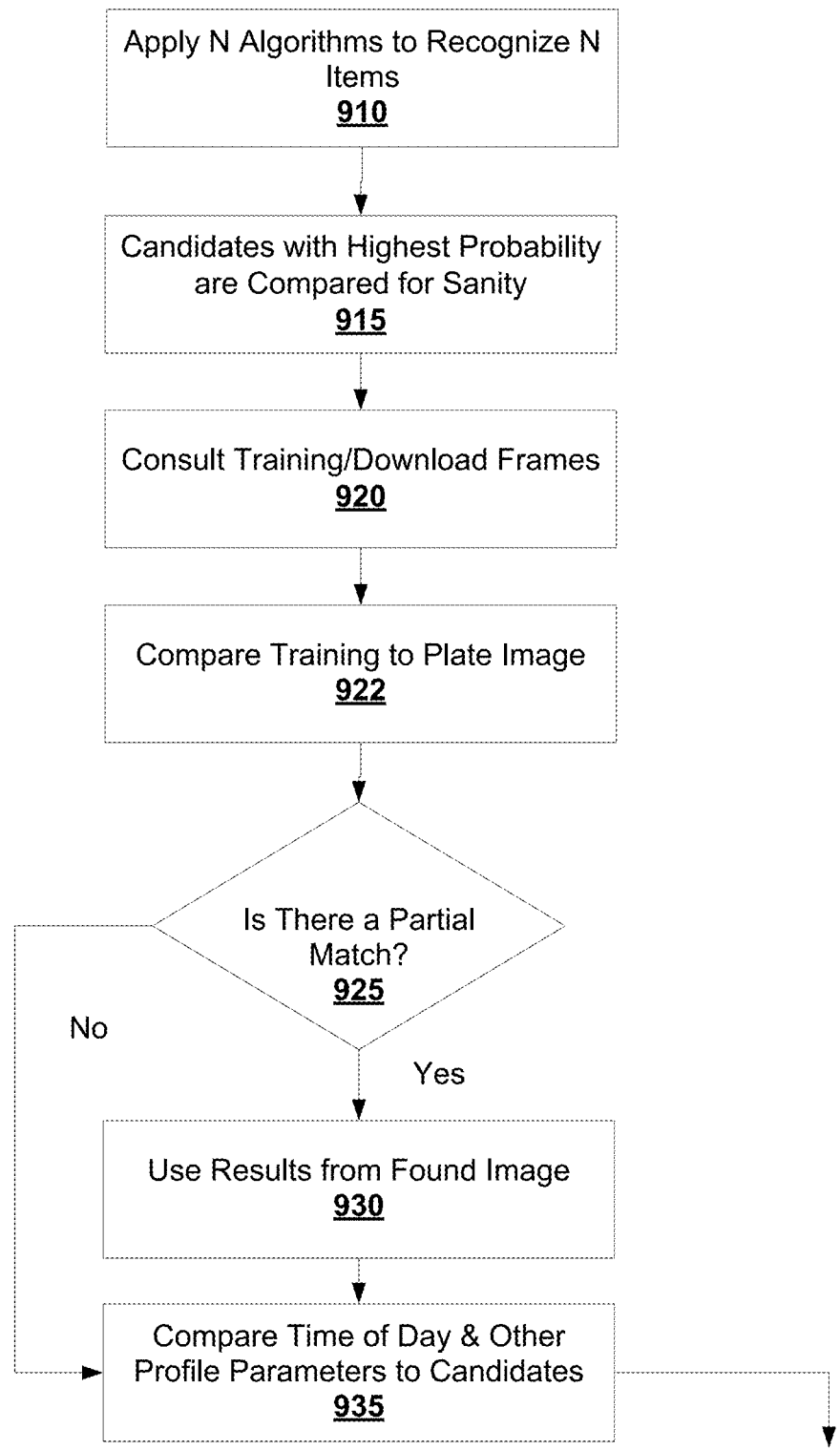
FIG. 9 is an exemplary flowchart of the Plate Analysis module in an exemplary embodiment.
Figure 9:
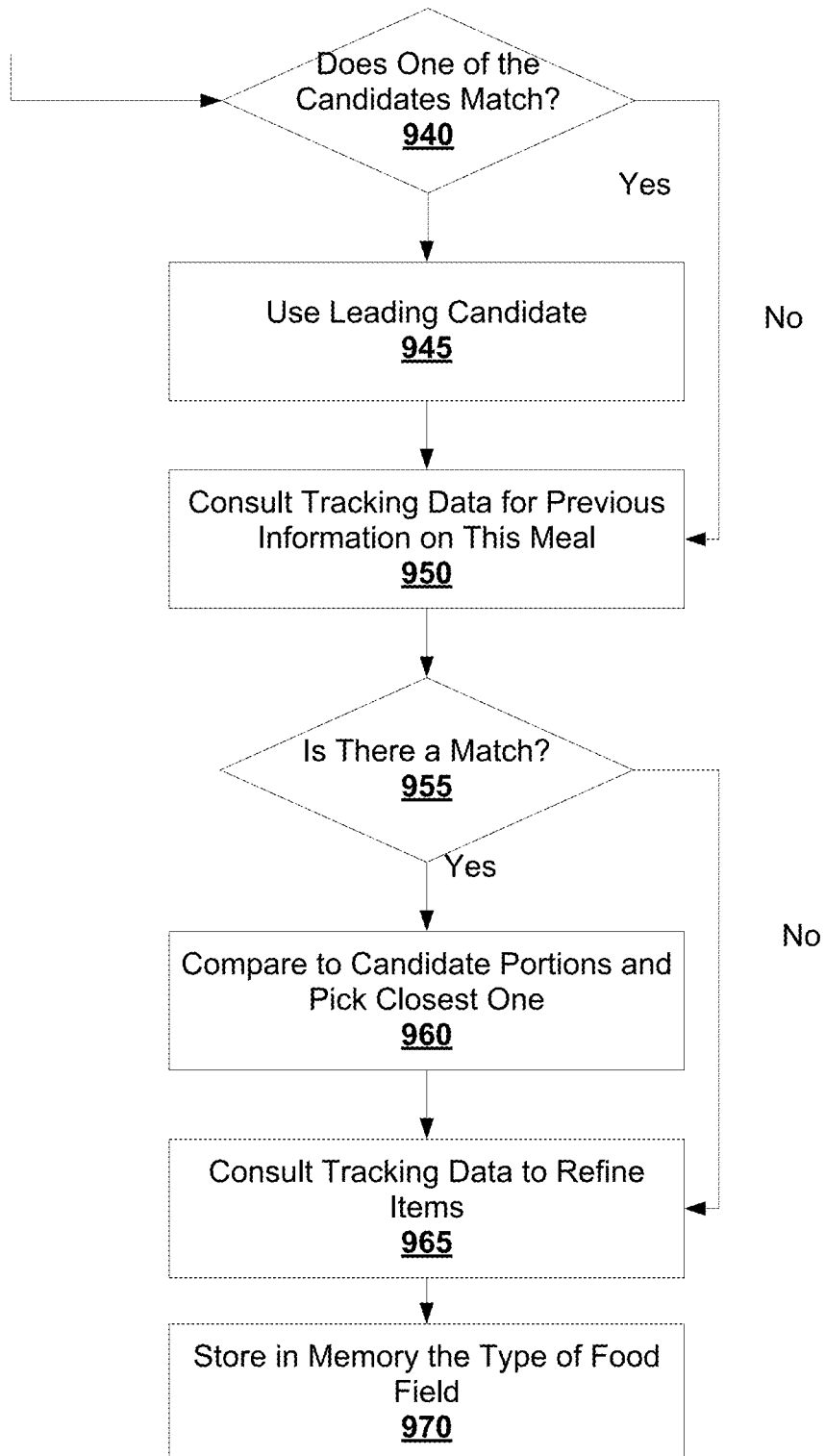

FIG. 9 provides a high level flowchart of the Plate Analysis Module in an exemplary embodiment pertaining to Plate Analysis modality. In step 910, the System applies the N algorithms (see FIG. 8 above) devised to recognize one of N Food types. For instance, to determine if there is beef steak on the plate. In step 915, for example, the 7 most likely food types (7 as an example) are compared for sanity. The Sanity check makes sure that the User is not eating beef steak, chicken, hamburger, and hot dog together. There should be some balance between the food types, as an example, beef steak and potato fries are good. In step 920, the System loads the Frames stored in the system (training/downloads), and utilizes the Frame Matcher sub-module to compare them to the plate image (step 922). There are many methods in the state of art of doing fast comparison of images using, for example, locality sensitivity hashing indexing methods. If there is a partial match (step 925), the System uses the result from the found image (step 930) and goes to step 935. If not, the System skips to step 935. In step 935, the System consults the profile of the User and also the System compares time of date, day of week, day of year and other parameters to the possible results. If one of the results conforms to the User's profile (step 940), then this result is the leading result (step 945). In step 950, the System consults the tracking data, to see if it has prior knowledge on that meal, like an order in a restaurant or a menu (see tracking section). If that is the case (step 955), the System compares that data to any of the candidate portions and pick the closest one (step 960). Otherwise, skip to step 965. In step 965, the System consults the tracking data, to refine further some items (e.g., regular Coke or diet Coke). In step 970, the System stores in memory the type of food fields.

Plate Frame Matching

In an exemplary process the System compares between known Video Plate frames (from training and downloads as described above) and the current Plate Frame to deduce the correct Food types for objects on the plate. Every known Frame has a set of records called Portions associated with it, and each Portion has a field of the Food Type.

The heuristic matching will be conducted between the respective frames. The locality sensitivity hashing indexing methods, for example, as described in United States Patent Application Publication No. 20090216755 can be used.

The matching yields one of multiple options:

1. New Plate frame—can be indicated by the User in training. In that case, the User describes the Portions as described above.

2. Partial Plate match—can be indicated by the User in training Δt least one Portion is the same as in previous known Video Plate Frames (both food type and similar volume/weight). If it is training or manual mode, the User will describe all other Portions.

3. Quasi match—can be indicated by the User in training. In this case the type of food matches to one Portion's type of food, but not carries the same volume, or weight.

4. Full match—All Portions are matched.

Most cases that are done in Automatic mode will end up in New Plate Frame (i.e., nothing was identified), or Quasi match (some Portion food type was identified).

Food Container

In yet another embodiment of the present invention, the concept of food container is disclosed. A food container is a physical food containing unit (such as a refrigerator or food compartment), furnished with tracking facilities to track the intake and outtake of food items from the unit in a semi or full automatic manner.

As a non-limiting example, items stored in the food container, are tagged by a barcode or furnished with a RFID repeater. The food container unit is equipped with a processing device and appropriate barcode/RFID reader and thus can identify the food elements as they are being put into the unit. Identification of the food type may include for example the ingredient of the food items and its total weight.

Optionally the food container unit is also equipped with known User identification means disclosed in other embodiments of the present invention.

When the identified User takes a food item from the food container, the processing device may attach the food item nutritional data to the User. For example, User Calories account may be charged by the Calorie intake of the food item.

Further optionally, the food container processing device may identify a partial intake, when the User returns the food item back into the food container unit. This can be implemented for example by putting the food item on a weight measuring plate, which can detect the weight differences of the food item between being taken out and returned to food container. Another partial detection option is to perform a computerized visual inspection of the returned food item. For a partial intake, the processing unit will adjust its nutritional data accordingly, for example, by charging the User with a reduced Calorie intake, based on the proportion of the actually consumed food.

Further optionally and in accordance with the current embodiment, the food container unit processing device may control the locking of the unit. For example, if a given User has exceeded his/her recommended daily Calorie intake quota, the food container will be locked for him, he/she not being able to open the container till the next day. The food container may also be equipped with a communication device to send its data to other units in a distributed network.

Figure 10:
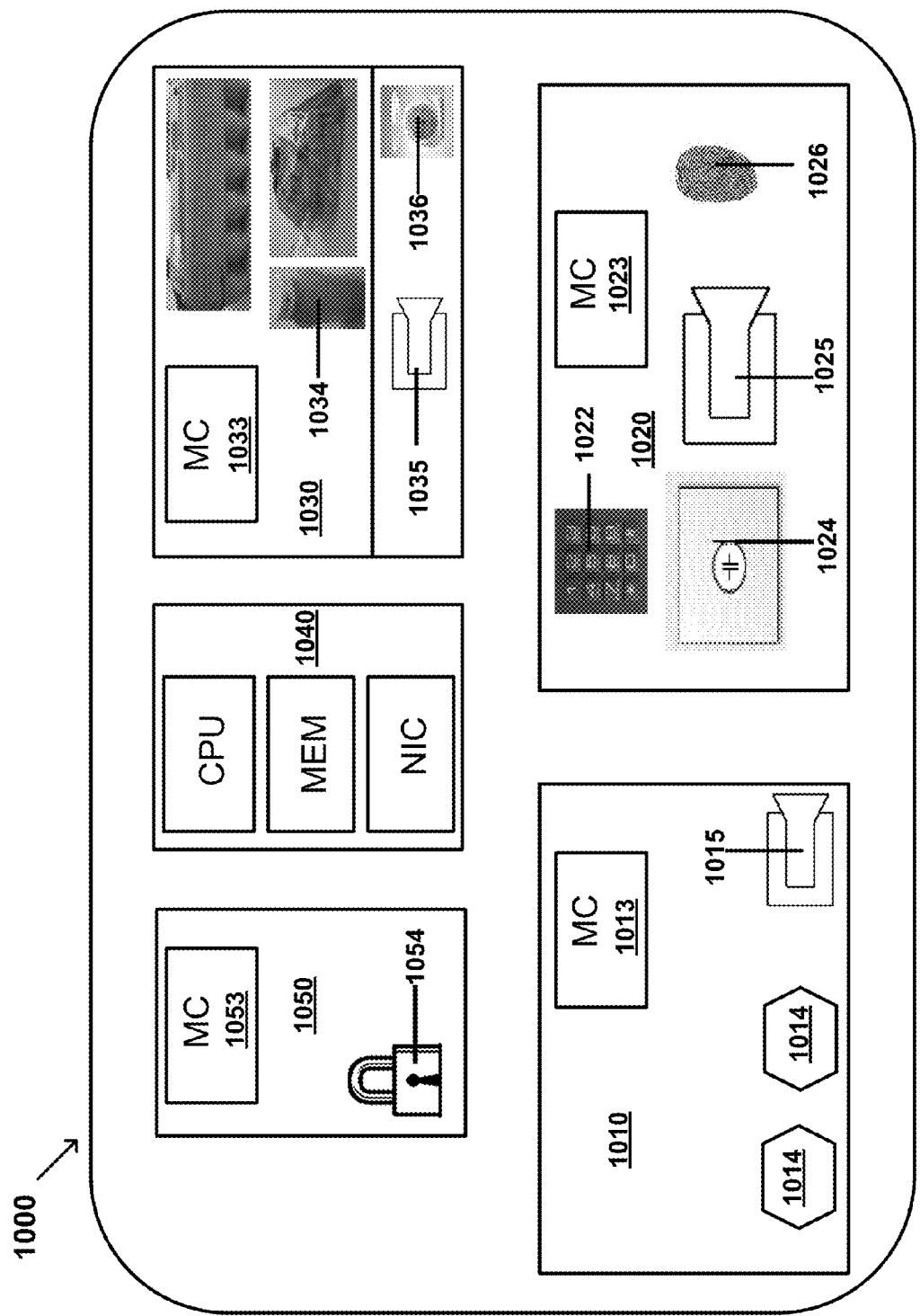
FIG. 10 provides a description of an exemplary apparatus of a Food Container.

FIG. 10 depicts an exemplary food container apparatus 1000. An exemplary food container apparatus 1000 may include:

(a) A Food Identification Unit-FIU (1010) for identifying food items being taken in or out of the apparatus, may further comprising a Micro Controller (MC)—(1013), which controls the operation of the elements of this unit and communicates with other units in this exemplary apparatus, a plurality of Barcode and/or RFID readers/controllers (1014) for identification of codes on food items, and a camera (1015), which may provide a visual inspection for food item identification.

(b) A User Identification Unit—UIU (1020)—for identification of the particular User currently using the apparatus may also comprise a Keypad (1022) allowing the User to enter an identification code for identification, user authorization and setup, a Micro Controller (MC)—(1023), which controls the operation of the elements of this unit and communicates with other units in this exemplary apparatus, a Microphone and audio controller (1024)—allowing audio based biometric User identification and optionally interpretation of vocal commands and/or description of food items. User identification may also be provided by a visual inspection via a camera (1025) and/or fingerprint reader (1026), either separately or in tandem by using multimodal biometric identification, based e.g., on audio and/or video and/or finger print and/or any other known biometric identification means and procedures.

(c) A Food Store Unit—FSU (1030)—For storing food items (1034) and estimating its volume and/or weight both for the initial state and/or after a partial intake. The unit may further comprising a Micro Controller (MC)—(1033), which controls the operation of the elements of this unit and communicates with other units in this exemplary apparatus, one or more camera(s) (1035) and/or weight measurement device(s) (1036).

(d) A Main Processing Unit—MPU (1040), which may include a processing device such as a Central Processing Unit (CPU), one or more memory (MEM) devices (in volatile and/or non-volatile form), a storage device (not shown), one or more communication bus(s) for internal and external communication (not shown), a communication device such as a NIC (Network Interface Card) for interfacing with external entities over any wired and/or wireless network, User interface devices (e.g., LCD screen, mouse, keyboard—not shown) and one or more software modules for the purpose of control and communication with internal units, external entities, data processing and User interfacing.

(e) Access Control Unit—ACU (1050)—Access to the unit might for example be limited to identified Users only, to identified Users provided that they have not exceed their predefined Calorie intake or other nutritional limitations, or unlimited. User might be further classified e.g., to regular Users and administrators, where e.g., administrator may open and access the unit without any limitations and have setup access rights, which a regular User would not have. The unit may further comprising a Micro Controller (MC)—(1053), which controls the operation of the locking element(s)—(1054) of this unit and communicates with other units in this exemplary apparatus.

Bite Generation

The Bite record generation uses the following observation. Users know what they are eating, but they are not good in determining the volume/weight of what they are eating. The following double heuristic will get this goal in an indirect way. Users or Video Analysis may not be good in determining what volume/weight we eat in each Bite of food, but Video/Audio Analysis is very good in determining how many Bites we actually eat in a meal. The System already knows what is the type of food is in each Bite, and the System knows quite a bit about the User (from training, from his profile, and from his BMR), the System can deduce the Volume/Weight that a specific User can put in his mouth in one Bite per food type. More than that, the System can determine the length of time of the chewing of the Bite, and figure from a range of possible Volume/Weight if that Bite volume/weight is in the high end of the range or somewhere else.

The System also knows what was on the Plate before the User started eating, and what is left on the Plate (assuming the Plate was not shared). The System can compare after each Bite, the volume/weight that the System deduced (based on the chewing time), versus what is left on the Plate compared to what was there before the Bite. Alternatively, the System can do this once only at the end of the food process state. Both heuristics taken together gives us the volume/weight in a very accurate way.

The main issue the System needs to overcome is that the camera may not be able to point directly to the mouth. The Scenery may contain a utensil, cup or hand moving food toward the mouth, but not show actual mouth movement (chewing). Worse, when a User speaks or swallows its own salvia, there are lips moving that may be confused with food chewing' lips moving. The System needs to differentiate between both cases (chewing and talking) Sometimes, the User may talk while he is chewing, which makes the chewing process longer for the same amount of Bite volume.

The System is able to differentiate between User's voice and food noise using classical Fourier transforms sub band filters and estimation of Signal to noise Ratio. The typical sound of chewing food has an audio frequency pattern that is identifiable and distinguishable from human voice. As the System uses a state machine (as described above), it is aware when the User starts food intake process, and only then it can apply voice processing methods to determine the time the User is swallowing the Bite.

Figure 11:
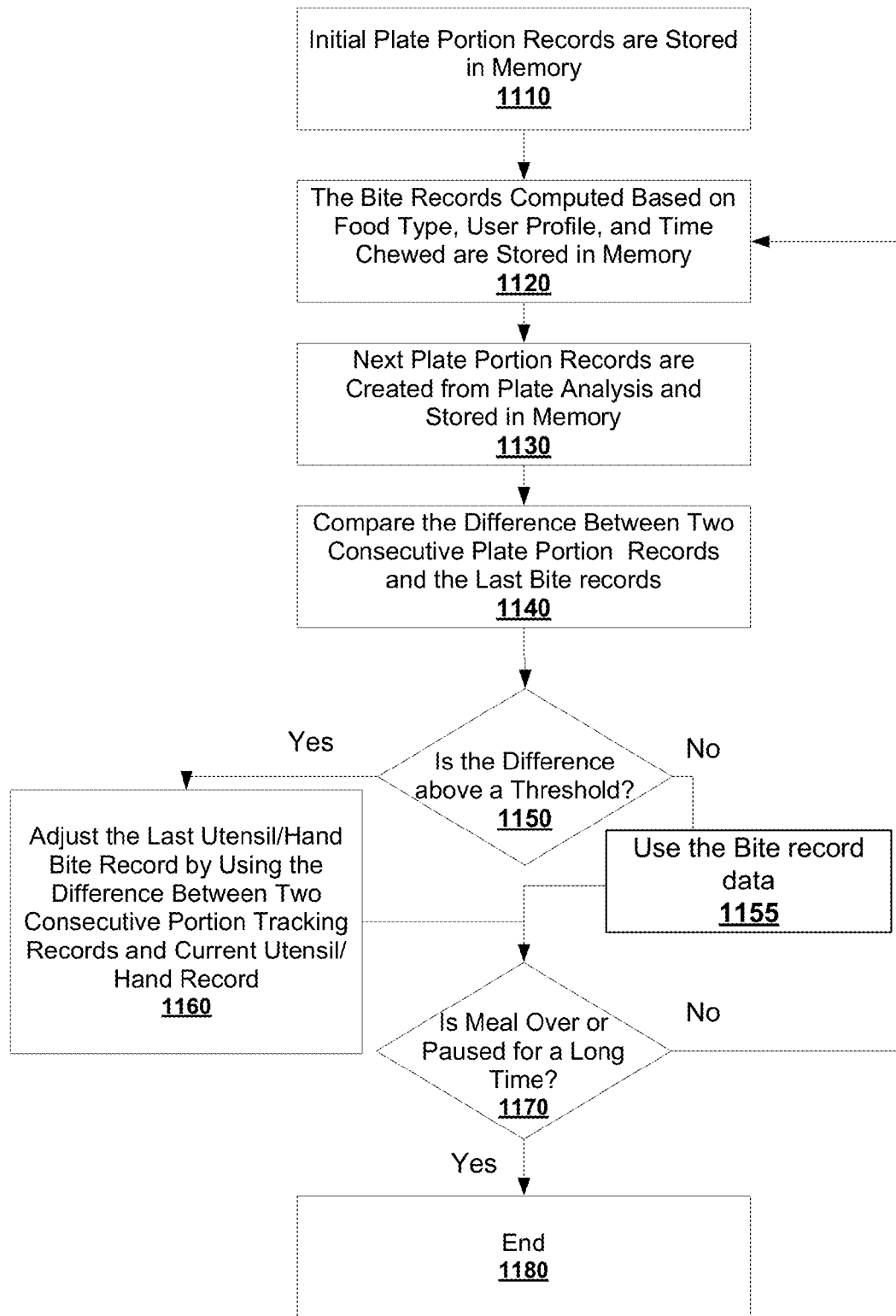
FIG. 11 is an exemplary flowchart of the actual food intake process.

FIG. 11 describes the flowchart of the actual food intake frame analysis (Bite generation sub-module). Notice, it is done in the simple case of one User eating from one plate. The more complex flowchart that describes multiple people eating from the same plate is similar in concept, but requires a more complex method.

Referring to FIG. 11, in step 1110, the initial Plate Portion records created by the Plate Analysis are stored in memory. The analysis of the food type was described earlier. The volume of each food type on the table can be computed using a range camera, and/or using similar methods as suggested in U.S. Pat. No. 8,345,930, which did not suggest using a range camera.

In step 1120, the Bite records are computed based on User profile, Time chewed (from a Fourier analysis described herein above) and from the actual food type taken into mouth as stored in memory. Note that the System can use visual analysis of the User's mouth activities and/or Fourier Audio analysis of the User's mouth activity by using a focused microphone pointing to the User's mouth, and/or embedded chip in the User's mouth or any other similar method, and/or combination of the above.

In step 1130, the next Plate Portion records are created from the Plate analysis are stored in memory (see how it is done in step 1110).

In step 1140, the System compares the difference between two consecutive Plate Portion records and the last Bite records.

If in step 1150, it is determined that the difference is above a threshold, then in step 1160 adjust the last Bite record by using the difference between the two consecutive Plate Portion records and also the current Bite record (averaging or any other statistical combination). Then go to 1170. Otherwise, in step 1155, use the Bite record data and go to step 1170.

If in step 1170, the System concludes that the meal is either over or paused for a long time. If not, the system moves back to step 1120. Otherwise, the meal ends in step 1180 and the Bite records are all generated.

Notice that there are two variations to this method. The first as described in FIG. 11 computes for every Bite the difference between the Plate Portions before and after, and picks either the difference as the volume, or the Bite size as the volume or some other statistical combination. A second variation calculates the Plate Portions one time before the meal, then accumulates all the Bites, and compares the summation of Bites to the difference between the Plate Portion before the meal, and the Plate Portion after the meal.

The System can use both variations and decide on the volume based on a statistical combination of the volumes calculated by using both variations.

Hand Analysis

Hand Analysis is the process of analyzing in the most simplistic way what the User is eating, when the food is actually on the User hand. An example is a User eating a peach.

Simple Hand Analysis

The Simple Hand analysis has two parts:
1. Identifying the food type in the Hand.
2. Identify the volume/weight of that food item.

We now assume the found pattern state is a Hand. Typically because of hand anatomy, there can be only one item in the Hand. We assume this is the case, and the task is to detect what it is.

Figure 12:
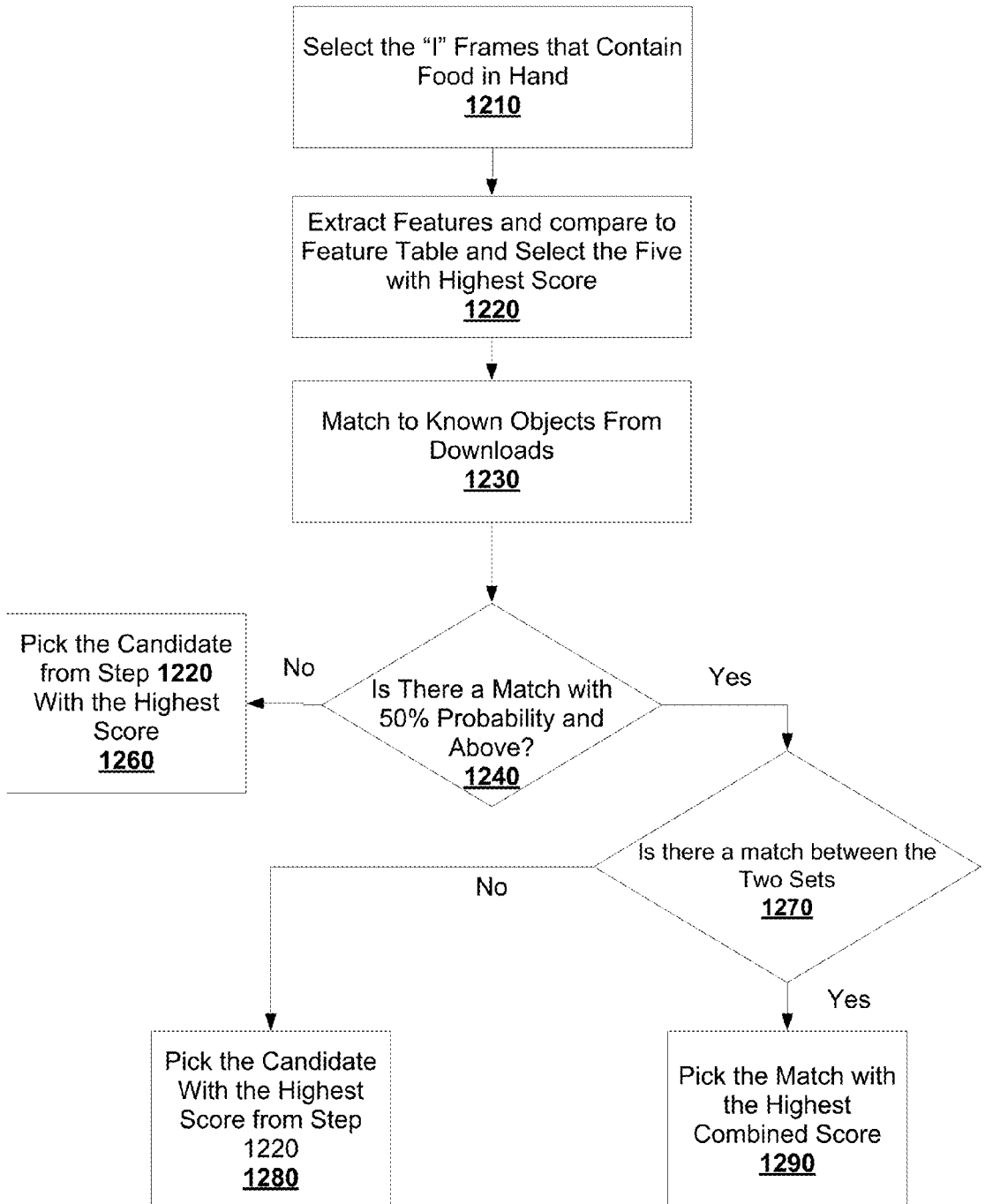
FIG. 12 is an exemplary flowchart on the operation of the Hand Analysis module in an exemplary embodiment.

See for example, FIG. 12. In step 1210, the System selects the "I" frames that contain food in the Hand. In step 1220, we run a similar algorithm as described in FIG. 8, which uses a table of all typical foods that can be in one hand, and we locate the five objects (five as an example) that have the highest score. In step 1230, we match the objects to all downloaded objects using the Frame matcher sub-module, which is similar to what was discussed in Plate Frame Analysis. In step 1240, we check if there a match with 50% probability or up. If there is no match, in step 1260, we pick the candidate from step 1220 with the highest score. If there is a match, then in step 1270, the System checks if there is a match between the two sets. If there is a match of one or more, then we pick that match with the highest combined score (step 1220 and step 1230) in step 1290. Otherwise, in step 1280, we choose the object with the highest score of step 1220.

After deciding the food type, we check the volume in the Hand frame object, based on the number of Bites that the User conducts (and for each Bite an analysis is done as described in FIG. 11). The summation of the volume/weight of all the Bites, gives us the volume/weight of the Portion.

A variation to that volume measurement uses the fact that most items that fit the Hand are standard, and based on the User and location; we can tell how big they are. For instance, if a User is detected eating a biscuit and he is located in the USA, for example, then the biscuit the User is holding has a different size than a biscuit that he buys in France. A table containing thousands of standard items per location can be used to calculate the volume/weight of what the User is eating from his Hand.

Tracking Sceneries

The food intake Scenery describes the process of the actual food intake. The Sceneries that were recorded up to several minutes (System configured) are considered to be potential Tracking Sceneries. The following figures will describe several non-limiting examples illustrate the information the System can extract from tracking the User before he actually eats.

Figure 13:
FIG. 13 describes an exemplary embodiment of the User at a restaurant.

Referring to FIG. 13, a User is in the restaurant or a bar, and the Tracking Scenery contains one or more of the following:
1. A menu—that may even describe the Calories (Frame)
2. A Waiter—describing the offerings (Audio Clip and its transcription)
3. The User himself ordering what he wants (Audio Clip and its transcription)

Those Tracking Sceneries contain Tracking records (to be described herein below) that help assist the System in deciding the actual food intake. In the training phase, the User assists the system in classifying the Tracking Sceneries. In addition, the User compares between the output the System deduces (Tracking Records) and the actual.

Similarly, a Scenery in the User's home dining table may contain one or more of the following:
1. The Cook describing what is there (Audio Clip and its transcription)
2. The User ordering what he wants (Audio Clip and its transcription)

Similarly, a Scenery in a Bar B Q setting may contain one or more of the following:
1. The Cook describing what is there (Audio Clip and its transcription)
2. The User ordering what he wants (Audio Clip and its transcription)

Figure 14:
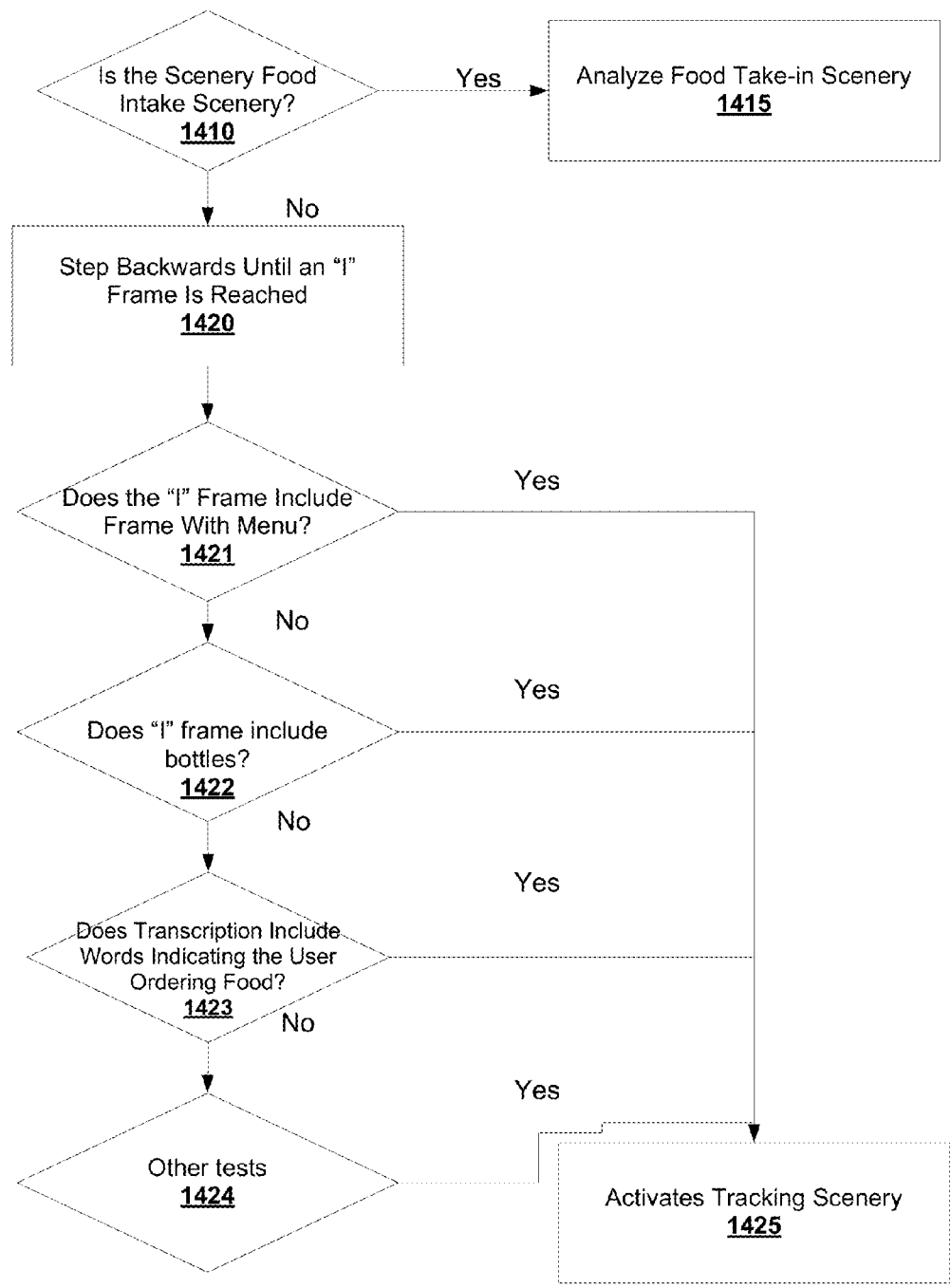
FIG. 14 provides a flowchart on the operation of tracking scenery determination logic in an exemplary embodiment.

Refer now to FIG. 14. Step 1410 determines if the current Scenery is a food intake Scenery. If it is, then Step 1415 analyzes food intake Scenery (see, e.g., FIGS. 5-9). If not, in step 1420, the System traverses backwards (from the beginning of the food intake Scenery) frame by frame till it reaches an "I" frame. If so, the System then executes in steps 1421-1424 various tests to check if that Scenery is a tracking Scenery. Here are some non-limiting test examples:
1. A frame that contains a menu is detected
2. A frame that shows bottles used for pouring into cups.
3. A transcription (associated with the audio clip) that includes keywords that indicate that the User is ordering some food.
4. Many other tests If the System finds an I frame that passes one of those tests, then in step 1425, the Scenery is labeled as a tracking Scenery.

The tracking process uses the Frame Matcher sub-module (see above) to compare the "I" frame to previous known frames (from training) Matching uses classical Scene analysis techniques such as locality sensitivity hashing indexing methods where the "I" frame passes segmentation and a labeling process that defines several big segments from a finite set of objects (e.g., restaurant table setting, Bar B Q, User's Kitchen, User's dining table). All training "I" frames are preprocessed and the list of Plate Portions are attached to each frame. If the current "I" frame is recognized, then it will get the Portion Plate records from the Training "I" frame.

Figure 15:
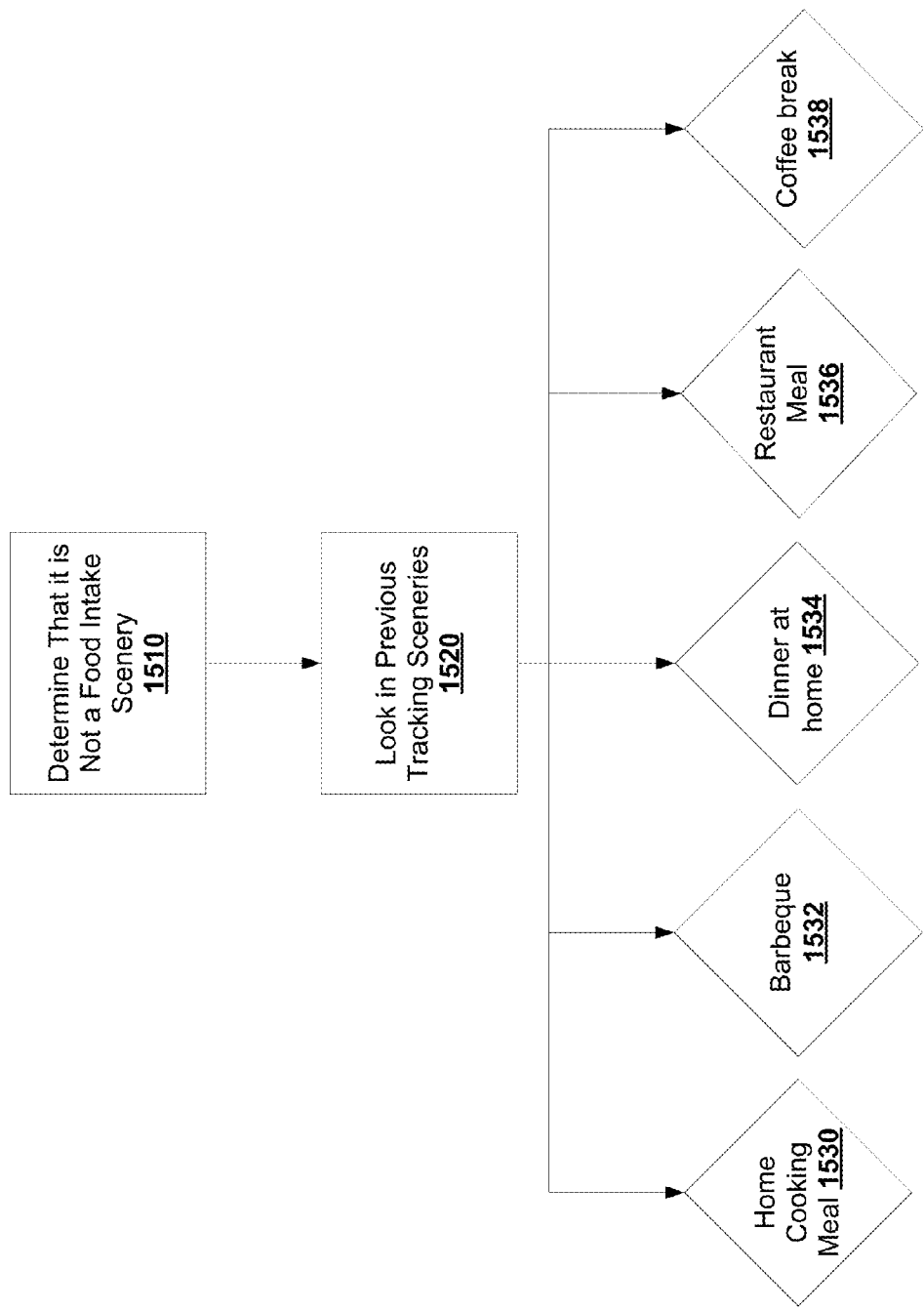
FIG. 15 describes the use of tracking sceneries in food intake analysis.

FIG. 15 describes the use of tracking sceneries in food intake analysis. In step 1510, it is determined that we are not in a food intake Scenery. In Step 1520, we go through previous tracking Sceneries. In steps 1530-1538, we query each scenery if it is home cooking, Barbeque, Dinner at home, Restaurant, Coffee break, and others. We may get more specific data, like, for example, Japanese restaurant. This specific data as well as their associated Audio transcript and Plate Portions will be useful in analyzing the food type as shown in the examples below.

Use of Tracking Sceneries

The Analysis of the Food Tracking gives some clues on the food types. Here are some examples:
1. If the User is in a Restaurant setting and the System tracks a menu image, it can read the items in the menu, and at least know the set of possible food.
2. If the User is in Restaurant setting, the audio transcript of the order can be analyzed to decide what the User orders.
3. If the User is in a Restaurant and the System can identify that it is a Japanese restaurant, it can limit the menu to Japanese food types.
4. If the User is eating at home, the System can analyze the Audio transcript of what the cook of the house prepared.

Figure 16:
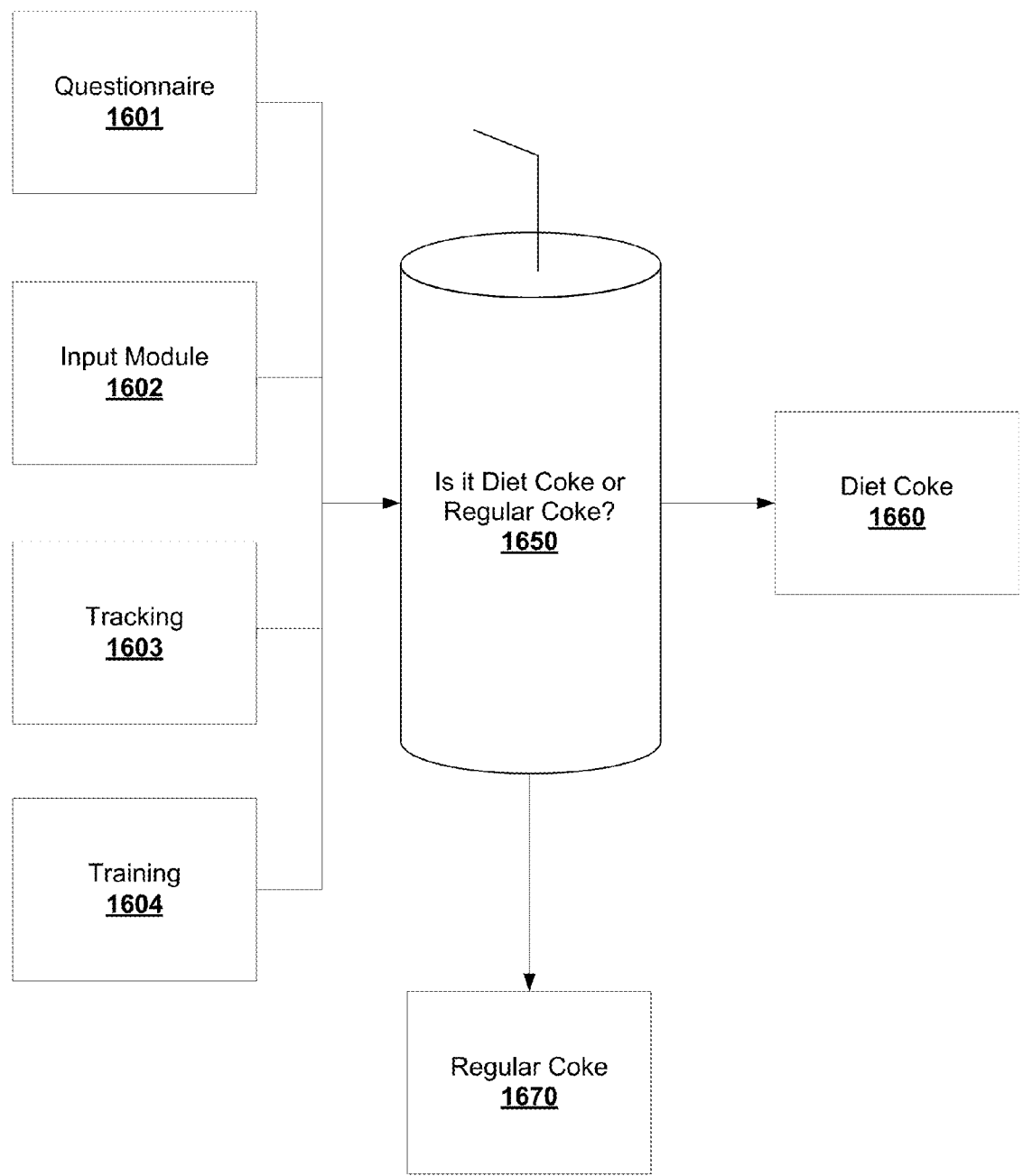
FIG. 16 discloses an exemplary determination between diet Coke and regular Coke.

In particular, FIG. 16 shows the process of analyzing a cup of drink to determine if it contains Diet Coke, or regular Coke in steps 1601, 1602, 1603, 1604, 1650, 1660, and 1670. Both cups look to the laymen eye or to a camera exactly the same. Nevertheless, a cup of regular Coke will include 100-250 Calories, depends on the size, which we can easily extract, as described above, and a cup of diet Coke will include 0-2 Calories, but, maybe other harmful ingredients to some Users. The Input Module can be used to query the User what actually is there. The Questionnaire and the specific User' profile can indicate that the User will normally choose diet Coke or regular Coke.

As described above, in one embodiment, the User gives his preferences when he starts using the system, a one-time operation. We can then know that the User prefers, or insists on diet Coke. If the User marks "insists on diet Coke" that will be sufficient to deduce that the cup is diet Coke.

In addition, as the System has the Tracking Scenery before the User poured the Coke into his cup, the System can detect the frame that contains the bottle, which was the source of the drink. Either by RFID signal, or by scene analysis, or by any other appropriate mean, the System deduces that the bottle is Diet Coke or regular Coke, and from that the system is more positive that the cup indeed had Diet Coke or regular Coke.

Another example is eating in restaurant. Obviously, the User does not pour the Coke from a bottle (in one case), but he is served. The tracking Scenery contains a transcript where the User is asking the waiter to bring him Diet Coke. From that transcript the System can deduce that the User drank Diet Coke.

Simple Volume Measuring

Figure 17:
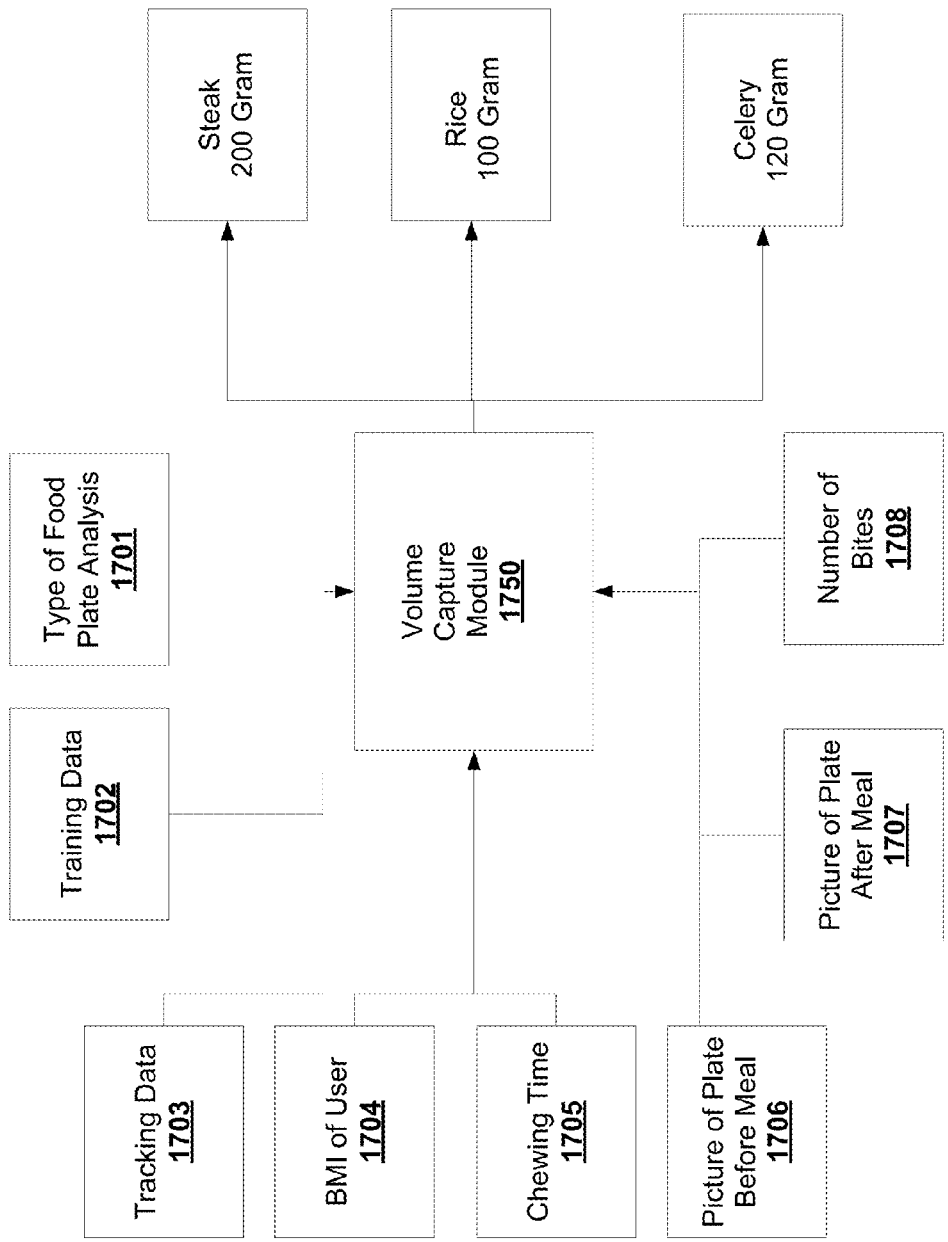
FIG. 17 is a schematic block diagram of an exemplary Volume Capture Module.

FIG. 17 provides a schematic description of the Volume Capture Module. The Volume Capture Module 1750 receives input from at least one sensor and at least one source of data and generates a set of coherent data volumes for the Plate Analysis Module (and the Hand Analysis module).

Some of the non-limiting parameters that are used to determine the volume include:

1701 The type of food taken from the Plate Analysis (or from the Hand Analysis)

1702 The training information, when the System has actual data from the User on a similar scenario

1703 Tracking data

1704 The weight and especially BMI (Body Mass Index) of the User

1705 Chewing time of each Bite

1706-1707 The actual picture of the plate, before and after the meal (and actual Bite eating)

1708 Number of Bites

The Volume Capture Module determines the volume and/or weight of each food type that was consumed from a plate.

It is a known fact that fat people eat faster than thin people. In most cases, fat people eat more than thin people, but not in all cases. Time measurements are easy and very accurate. Thus, the System can measure the time the User is eating from his first bite to the last one. As the System knows the User's weight and BMI (Body Mass Index) the System can extrapolate the amount of food that he ate. The System knows the type of food, as we assume that eating lighter food is easier than heavier food. For instance, eating Spaghetti is faster to eat than a hamburger.

The main assumption is that the User eats regularly and the same portions. A Camera and/or a microphone can track relatively easily the number of actual Bites and the Camera can analyze what was on the Plate (Hand) and what was left after the User ate a Bite.

As we observed, in training, the User feedback is very reliable on what he is eating (Food Type), but much less reliable on the volume/weight. However, there are certain circumstances when the User is more reliable. Some non-limiting examples include:

1. Packaged food—When a User eats from standard packaged food, it is relatively easy to determine (by the User) what was the weight of what he just consumed.

2. Restaurant meals—In many restaurants it is very common to write on the menu the weight of the item.

3. Common food—Many type of foods come in standard size.

As described in FIG. 11, embodiments of the present invention may track the number of Bites that the User consumed, and the time it takes to chew each Bite and as the System knows some data about the User, it can figure how much volume/weight is in each Bite and then add them up. In Addition, if the source of the food is from a Plate, the system can capture the image before and after and figure how much was originally there, and how much is left at the end, and then compare both results.

Auxiliary Weight Measurement for Estimating Food Intake

In yet another exemplary embodiment, an auxiliary User weight change measurement unit facilitates the ability to estimate the amount of food intake by a User. In accordance with this embodiment, the User is for example sitting on a chair, furnished with a weight measurement device.

The chair's weight measurement device keeps tracks on the weight changes while the User is sitting on the chair being presumably eating. The weight change tracking starts at the event of the User start sitting on the chair (identified by the sharp increase in weight) is automatically disabled when the User leaves the chair (identified by the sharp decrease in weight).

The chair is further equipped with a processing device, which controls the operation of the measurement device, the generation of weight change record, and communication with other devices described in other embodiments of the present invention.

Typically this weight measurement data is integrated with other User food intake data to produce a more accurate assessment of food intake amount by volume and/or weight. Optionally, the chair may be further equipped with User identification facility for identifying the User in a semi or fully automatic manner. The chair may also be equipped with a communication device to send its data to other units in a distributed network.

Aggregator

This System calculates the actual food intake, and not what the User was served, as there can be a discrepancy between those two items. More than that, the eating process is done in steps. So, assuming the User has a 300 gram beef steak on his plate, he is eating it piece by piece, and he may leave a portion not consumed. More than that, there may be a situation where the food on the plate is shared with other people on the table. In that case, the steak is consumed, but the User only ate a part of it.

Refer to Table 9, which is an exemplary data. The atomic Bites created during the meal are converted into set of Portion records reflecting the meal. The Aggregator eliminates all the intermediate records that were generated per the same food type, and aggregates for each Food Type only one Portion record. Notice, that eating is a complex process, and the User probably consumes multiple portions from his plate and from other sources, as well as drinking something.

The aggregator also calculates the actual time length of the meal (per that food type), and put it as a field. Notice, this is not the summation of the Bite chewing time length, as there are pauses between Bites.

Thus, the end result will look like FIG. 20, which describes the Food Portions and volume/weight that the User had for lunch.

| Date & Time | Food location | Food Type | Food Name | Volume Plate | Weight Plate | Time Length | Volume Consumed | Weight Consumed |
|---|---|---|---|---|---|---|---|---|
| 1 Aug. 2013 14:15:00 | Restaurant | Beefsteak | Fillet | 350 CC | 380 gr | 13 s | 37 CC | 30 gr |
| 1 Aug. 2013 14:15:07 | Restaurant | Beefsteak | Fillet | 291 CC | 330 gr | 17 s | 59 CC | 50 gr |
| 1 Aug. 2013 14:15:10 | Restaurant | French Fries | French Fries | 290 CC | 290 gr | 8 s | 35 CC | 30 gr |
| 1 Aug. 2013 14:15:15 | Restaurant | Non Diet Drink | Sprite | 220 CC | 220 gr | 13 s | 70 CC | 70 gr |
| 1 Aug. 2013 14:15:21 | Restaurant | Beefsteak | Fillet | 241 CC | 284 gr | 16 s | 50 CC | 46 gr |
| 1 Aug. 2013 14:15:25 | Restaurant | French Fries | French Fries | 250 CC | 255 gr | 10 s | 40 CC | 35 gr |
| 1 Aug. 2013 14:15:33 | Restaurant | Beefsteak | Fillet | 191 CC | 238 gr | 16 s | 50 CC | 46 gr |
| 1 Aug. 2013 14:15:40 | Restaurant | Non Diet Drink | Sprite | 130 CC | 130 gr | 16 s | 90 CC | 90 gr |

Sanity Check

Figure 18:
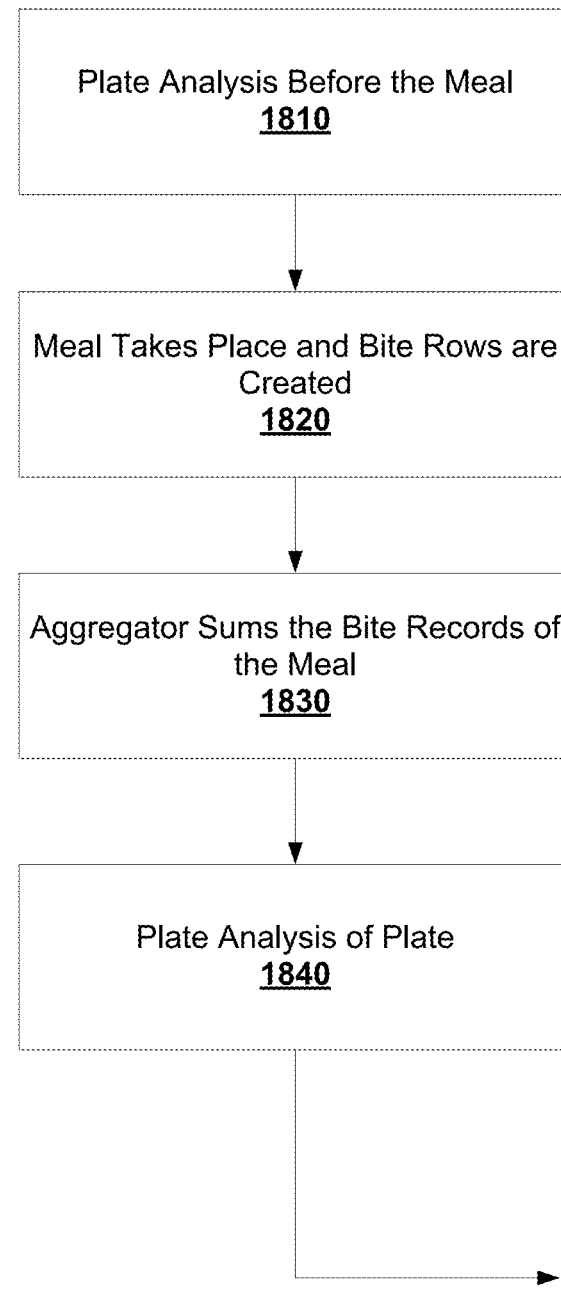
FIG. 18 is an exemplary flowchart on applying a sanity check after the aggregation process in an exemplary embodiment.
Figure 18:
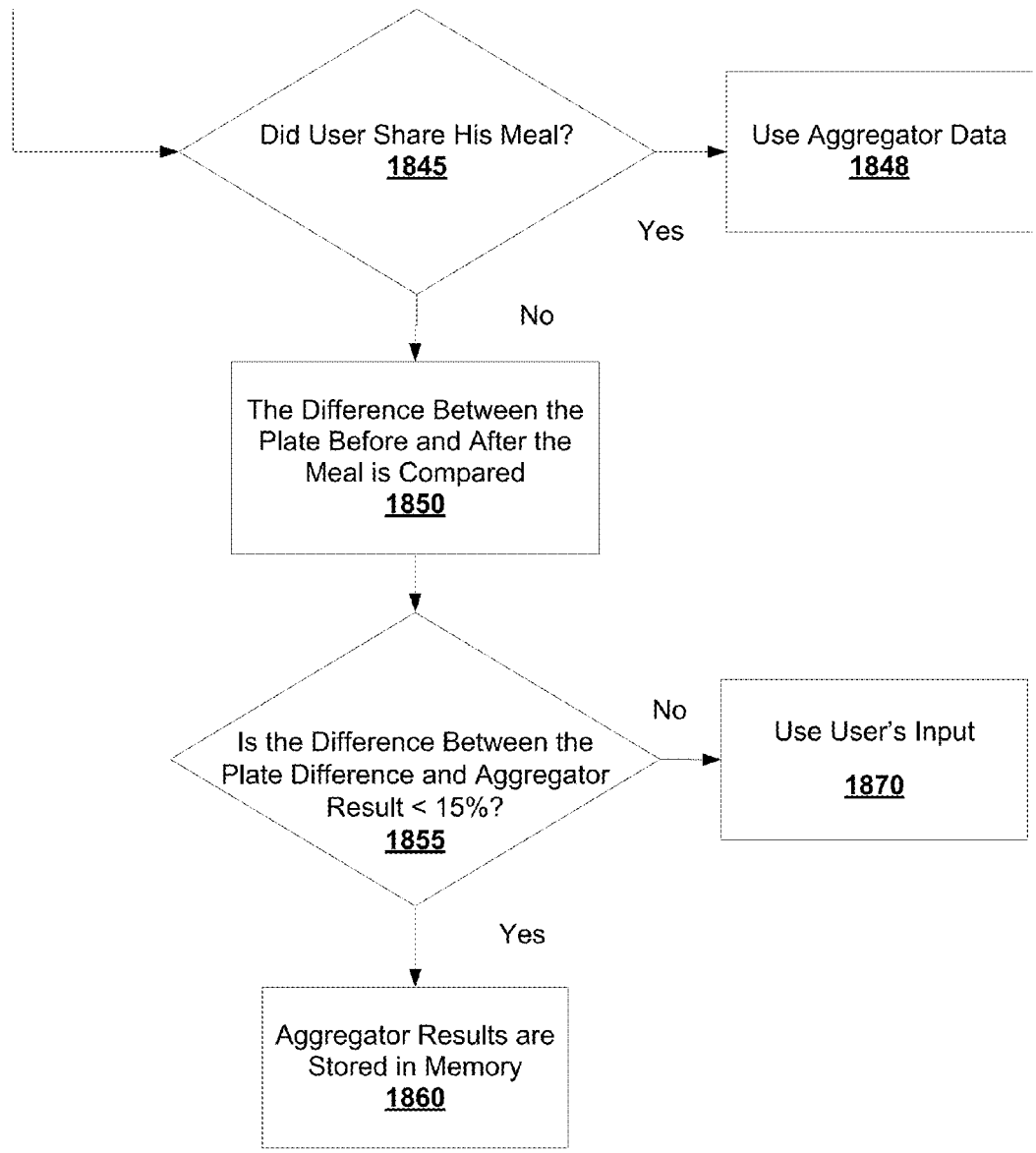

Referring to FIG. 18, which describes a flowchart of the process in an exemplary embodiment, in step 1810, the System conducts a plate analysis of the plate before the meal. In step 1820, the meal takes place, and Bite rows are created. In step 1830, the aggregator sums all the Bites to get the food portions of the meal. In step 1840, a plate analysis is done on the resultant plate. In step 1845, a check is done to determine if there was any sharing. If so, in step 1848, the aggregator data is used. If not, in step 1850, the difference between the Plate Portions before the meal and the Plate Portions after the meal are compared. If the results are different than that of the aggregator by less than 15%, then in step 1860, the aggregator results are stored into memory. Otherwise, in step 1870, for example, a beep is activated and the User is asked to verify.

Feedback Cycle for Food Intake Analysis (Training, or in Semi Manual Mode)

Figure 19:
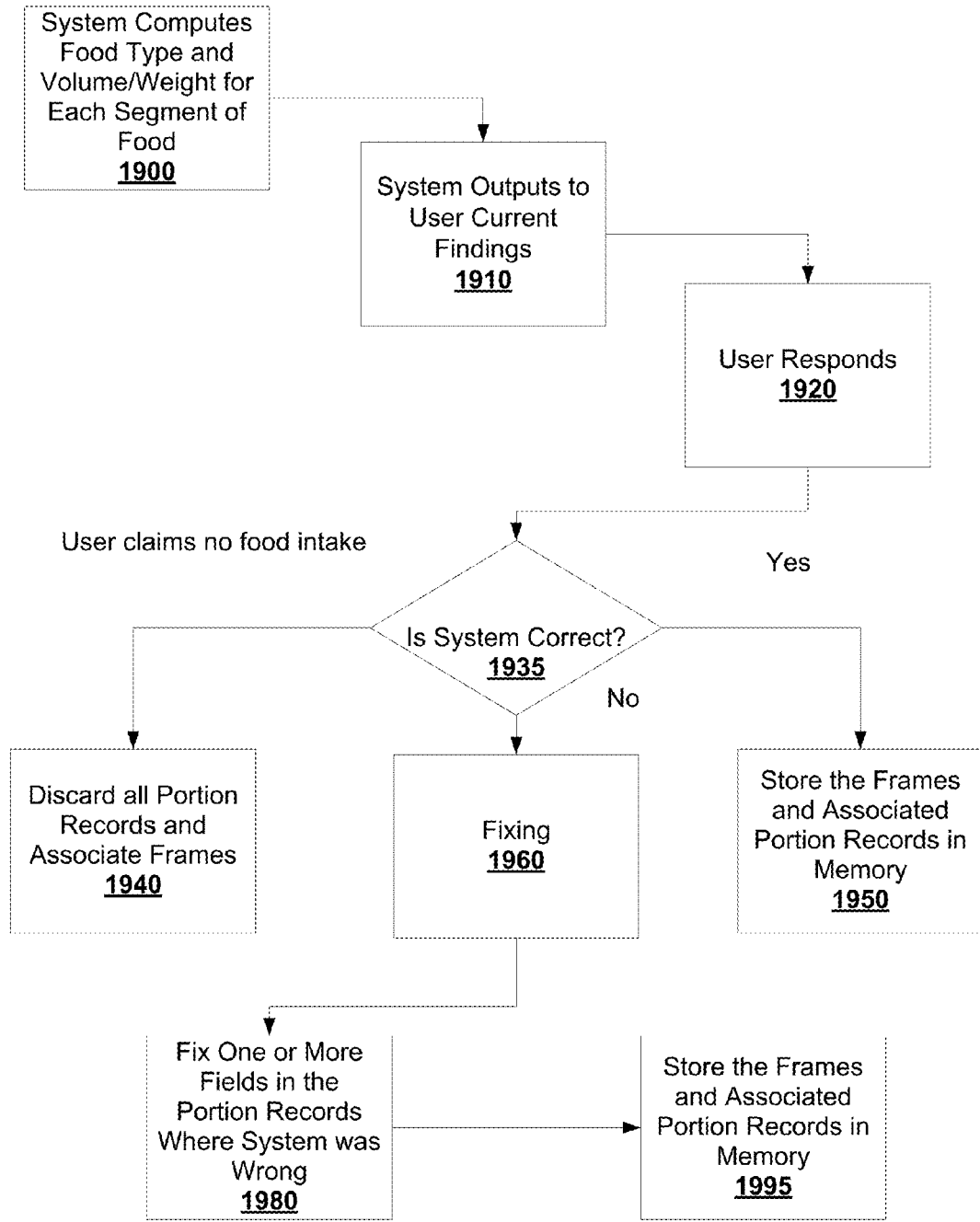
FIG. 19 shows a feedback cycle for food intake analysis.

FIG. 19 describes the feedback cycle for food intake analysis. In step 1900, the System computes Food Type and volume/weight for each segment of food. In step 1910, the System outputs to User its current findings in methods that were described above. In step 1920, the User responds (also using methods described above). If the system is correct (step 1935), the System stores the Portion records and associated Frames in memory (step 1950). If the user claims there was no food intake, all Portion records and associated frames are discarded (step 1940). If the user determines that there was food intake, but the System miscalculated, a cycle of corrections will take place (step 1960) where the User will fix, add, or delete one or more fields in one or more Portion records, where the system was wrong (step 1980). In step 1995, the correct Portion records and their associated frames will be stored in memory.

Monitoring

In an exemplary embodiment of the present invention a method is disclosed for monitoring food intake, where several analyzing activities can be programmed and activated. Here are some non-limiting examples 1. How many times the User has eaten during the day and what both in food type and volume/weight.

2. The timing spacing between the eating processes.

3. The daily amount consumed in Calories, all kind of ingredients and others

It is also known the advantage of regular timing food intake. The system will be able to monitor the User's eating practices, and gives the User a feedback when the User deviates from the procedures that the User decided to keep.

The system also monitors the User eating between meals, and gives him the appropriate feedback. Other monitoring activities as disclosed in all embodiments described above are also repeatedly conducted.

Calorie Balance Adjustments

In yet another embodiment of the present invention, User Calorie expenditure is monitored as well. Some measurement and estimation procedures are already provided by the existing art, for example:

a. Calorie expenditure estimation based on User heart bit rate measurement when the User is holding a workout device.

b. Calorie expenditure estimation based on measurement of the distance that the User has passed.

c. Calorie expenditure estimation based on measurement of number of steps the User has performed on a workout device (e.g., stairs).

d. Estimating the Basal Metabolic Rate—(Calorie expenditure at resting of the User), designated herein as BMR. There are non-User specific formulations known in the art for estimating BMR, such as Harris—Benedict equation or The Harris—Benedict equations revised by Roza and Shizgal, which provide some degree of accuracy for such estimation.

However, the existing art provides only an occasional limited measurement span, and fails to disclose an individualized and integrated Calorie expenditure measurement, estimation and tracking system.

The present invention, discloses additional procedures, methods and an integrated and individualized Calorie balance tracking system, which overcomes the stated above limitations of the existing art.

The current exemplary embodiment depicts steps of individualized Calorie tracking, by taking into account User specific information, such as anatomical and health information, such as can be provided by the following non-limiting list:

a) User BMI b) User % fat in body c) User % muscles in body d) Circumference of waist, hip, forearm, neck and other body organs.

e) Lean Body Mass of the User.

f) User Gender, Height Weight and Age.

g) User ethnicity h) User health data related to thyroid functionality i) User health data related to glucose levels and insulin resistance.

j) User rest heart rate and its changes as a function of body activity k) User rest blood pressure and its changes as function of body activity l) User body temperature and its changes as a function of body activity m) User blood type n) Genetic Related information (such as User's genome)

The User specific information as a whole, in part or any combination thereof, is integrated with non-specific User information related to Calorie information and activity measurement devices for constituting a comprehensive and individualized Calorie expenditure tracking sub-system.

The Calorie expenditure tracking sub-system may be further integrated with any Calorie intake measurement, estimation and tracking sub-system such as, without limitation, those disclosed in other embodiments of the current invention and generate a Calorie balance tracking system, where a measurement, tracking and estimation of the User Calorie balance, i.e., Intake versus expenditure is provided as a service to the User and/or a diet consultant and/or medical/paramedical stuff pursuant to User permissions and consent.

In the framework of the Calorie balance tracking system, both Calorie intake and expenditures are being monitored, measured and/or estimated. The User interface may include Calorie balance indications rather than just Calorie intake indications, for example the User may be informed that he/she has exceeded a predefined Calorie balance plan (such as e.g., losing 200 Calories each day), however if the User increases its Calorie expenditure by some physical activity, the system automatically sets the Calorie intake budget, accordingly.

Besides using the User specific information, for estimating individualized BMR or other individualized Calorie expenditure figures, the Calorie balance tracking system provides an additional merit by allowing a feedback corrected individualized BMR estimation.

It is known by previous research that two individuals having otherwise identical individual data, pertaining to steps (a)-(r) above may still have substantially different BMR figures, due to internal metabolism differences, which are not exposed through data such as Lean Body Mass, % fat in body, age, gender etc. In a similar manner, such two individuals may burn a substantially different amount of Calories while performing an identical workout.

In order to overcome this challenge the corrected individualized BMR estimation procedure uses the User Calorie balance tracking data to dynamically correct the estimated User individualized BMR for the User, by performing the following steps:

1) Estimate the User BMR

2) Track User Calorie intake by using, without limitation, methods depicted in embodiments of the present invention or elsewhere.

3) Track Calorie expenditure by using, without limitation, methods depicted in embodiments of the present invention or elsewhere.

4) Measure User weight differences over a period of time (e.g., one month), and compare the weight differences to the Calorie balance. A common conversion figure is 7500 Calories per one Kilogram. For example, if the User had lost 2 kilograms in is weight during this period, his/her Calorie expenditure is expected to be greater than the Calorie intake by 14000 Calories. If we get for example 10,000 Calories, the difference of 15,000−10,000=5,000 Calories will be designated as Calorie Balance Deviation (CBD); CBD can take positive as well as negative values.

5) Qualify the CBD results and the Calorie tracking procedures. Deviation from expected balance should be in a reasonable level, In addition Calorie intake and expenditure should be in a predefined expected range as well.

6) In case of a successful qualification, calculate a new BMR based on the previous BMR and the CBD of step (4) above.

7) Repeat steps 1-6 for the next tracking period.

In a similar manner it is possible to extract changes in the Calorie expenditure per unit workout.

Using two estimation periods, and solving a system of two linear equations and two unknowns (X=corrected BMR, Y=Calorie expenditure per unit workout), assuming that the User workout activity over that period can be measured, or otherwise estimated with a reasonable level of accuracy.

Changes in BMR and Calorie expenditure per unit workout can also be estimated, from the type and amount of workout performed by the User throughout the workout period, for example by measuring and/or estimating:

1) strenuously level of each workout 2) duration of each workout

3) Type of workout (aerobic vs. Non-aerobic)

By such a procedure, it is possible to estimate anatomical changes in the User body, such as increasing muscle mass, reduction in fat, which may lead to increased BMR and Calorie expenditure in workout. Likewise, excessive Calorie intake may be measured and/or estimated as well according to methods and systems such as those disclosed in the present invention, and cause a decreased BMR (per unit of weight) and Calorie expenditure in workout.

In an embodiment of this invention, the workout procedure of the user is being monitored by a set of sensors, measurement and interface devices to estimate and track the user's workout plan and is progress, estimate changes in calories expenditure and lean body mass, and provide online guidance and feedback for the user such as real-time calorie expenditure, affected muscles and strenuously level of the workout, possibly in a graphic modeling simulation form on a screen, and/or warnings in case the user has exceeded a safe level of exertion (based on user specific data) and might though be exposed to injuries or health damages.

The system may also provide a progress report following the training session.

Further within the teaching of this embodiment, the set of sensor may include one or more cameras and/or 3D vision sensor, which monitors and analyzes the user's actions and movements during the training, and possibly a communication channel with the workout device, which can provide information on the current actions of the user over the said workout device, such as the weight or resistance force into which the workout device is currently tuned to, and actions over the users over that device (e.g. number of times the user is lifting a handle).

Optionally, computer vision analysis software may monitor and recognize user's movements and actions in a 2 or 3D model space, and further estimate the force on muscles groups based on an anatomical muscle model.

The system may gather the visual analysis software data with information from one and more workout device via communication channels to provide an integrated real-time workout guidance and feedback as described above for this embodiment.

In an embodiment of this invention the system may also differentiate between Computed Calories and Actual Calories. The following will give two non-limiting examples:

It is assumed that Calories over consumption and short consumption are not symmetric. Many people observed that they had in one time over eaten X amount of Calories, which added to their weight, but when they removed the same X amount of Calories, that weight was not removed. It seems that there is a need for higher number Calories to reduce to compensate for Calories that were added. The System takes this asymmetry into account.

Ambient conditions at the time of food intake will take part in the actual Calorie consumption calculation, that also take into account the volume of liquid consumed by the User (including water embedded in standard food). In an exemplary embodiment, the System records per all location and per hours of days (24 samples per day as a non limiting example) the temperature and humidity in the location. This data, combined with the amount of liquid consumed, may modify the actual Calories consumed by the User.

Similar methods and procedures can be employed to track dietary related balance figures other than Calories. As a non-limiting example, glucose levels can be indirectly monitored through estimation of, for example, Glycemic load and Glycemic index, vs. Glucose unloading by the body through estimation of User specific Glucose sensitivity and measuring and/or estimation of User workout, which facilitates faster unloading of Glucose.

Another advantage of the Calorie balance tracking system is its ability to estimate another source of Calorie expenditure known as dietary induced thermogenesis (DIT) and also known as thermic effect of food, or TEF. Simply, it's the energy used in digestion, absorption and distribution of nutrients. It is one of the components of metabolism along with resting metabolic rate and the exercise component.

DIT may consume 5-30% of the Calorie intake, and thus is an important component in the Calorie balance measurement and estimation process, and therefore should be taken into consideration. However, existing art fails to do so in a computerized manner.

According to an embodiment of the current invention, we use estimation of Calorie intake, as well as the composition and/or ingredients of the foods to provide an estimate of the DIT related Calorie expenditure. The DIT related Calorie expenditure estimation will be added to the total Calorie expenditure figure and optionally to the balance provided by the Calorie balance tracking system. Without limitation, DIT figures might be taken into consideration as part of methods, procedures and embodiments of the current invention, such as the feedback based correction of the User specific BMR as stated above. Estimations of Calorie intake and its ingredients can be provided according to methods and systems disclosed in embodiments of the current invention or elsewhere, in manual and/or semi-automatic and/or fully automatic manner.

The following tables illustrate an exemplary DIT related Calorie expenditure estimation, tables values are given for illustrative purposes only, and may not reflect genuine or accurate figures.

Table 10 is an example of main food types' estimated relative DIT levels, as a percentage of Calorie intakes. As the reader may notice, there might be substantial differences between the different food types.

TABLE 10

| Food type | DIT % Level |
|---|---|
| Saturated Fat | 5% |
| Non-Saturated Fat | 12% |
| Simple Carbohydrate | 10% |
| Whole Grained Carbohydrate | 20% |
| Low Fat Protein | 30% |

There are some specific foods, which may increase DIT, without any relation to their Calorie content, but just as a function of its total amount. Examples of such foods are shown in Table 11.

TABLE 11

| Food type | DIT (cal burning per g.) |
|---|---|
| Chilly | 5 |
| Pepper | 5 |

Table 12 shows an exemplary DIT calculation of a given dish containing a spicy chicken and rice. Each part of the dish is separated to its ingredients and per each entry the DIT value is calculated according to its entry in exemplary Tables 10 and 11. The DIT can then be subtracted from the Calorie intake in order to produce an estimation of the net Calorie intake, with the consideration of the DIT.

TABLE 12

| Food Type | Weight (g) | Calorie Intake | DIT | Net Intake |
|---|---|---|---|---|
| Chicken | | | | |
| Total Weight | 150 | | | |
| Protein | 40 | 180 | −54 | 126 |
| Fat | 8 | 72 | −7 | 65 |
| Chilly | 2 | N/A | −10 | −10 |
| Sub-Total | | 252 | | 181 |
| Rice | | | | |
| Total Weight | 110 | | | |
| Simple carbs | 45 | 200 | −20 | 180 |
| Fat | 2 | 18 | −2 | 16 |
| Sub Total | | 218 | | 196 |

Distributed Nutrition and Calorie Balance Control

In yet another embodiment of the present invention, the User is provided with a distributed nutrition and Calorie balance, tracking estimation and management service. By "nutrition" or "nutritional" we refer herein not just to the intake of food, but also to various types of Calorie expenditure, including e.g., workout as well in some cases to User anatomical and health data.

According to the teaching of this embodiment, there is a plurality of measurement and/or interface and/or control devices interconnected over a computer data network.

Measurement devices in that respect may perform any measurement and/or estimation functionality of nutrition and Calorie intake, and/or Calories expenditure as depicted by other embodiments of the present invention or elsewhere. Measurement device are not limited for performing measurement functionalities per-se, and may perform in addition computational analysis as described in other embodiments herein, including but not limited to visual analysis of food intake, vocal analysis of food phrases, weight difference identification of food intake, estimation of food ingredients, visual character recognition of food related text, identification of text by RFID and/or barcode tags, measurements of User workout activity and bodily function.

Each measurement devices may provide a plurality of Nutritional Information Items.

A Nutritional Information Item may comprise nutritional related, food intake and calorie expenditure data such as (but not limited to): food intake by volume and/or weight, food type, calorie intake, nutritional composition of a food, percentage of actual food intake out of a given food unit, calorie expenditure (general or user adapted), work-out details, nutritional constrains and limitations, time based information on food intake or work-out procedures, user specific data for calorie balance adjustment. One or more Nutritional Information Items may be represented as a Nutritional Information Record on a computerized media.

In addition a device may contain User identification facilities, which may identify a User by biometric means (finger, Iris, voice analysis, face recognition and other method known in the art), by the User providing an access code and/or by the User providing an identification card to a card reader device, User manually inserting his details, and/or by any other User identification method.

Interface devices are used for entry of information and provide User indication, such as (but not limited to) methods and system disclosed in embodiments of the present invention.

Control devices may control the operation of other device in the system and the transport of data between various components of the service infrastructure.

A management unit providing means to gather a per-User nutritional information records (NIR) from the plurality of devices. Whenever the information is tagged by a User identification code of any kind, the management unit can associate each nutritional information record with a User information database and update it nutritional and Calorie balance data.

In addition, the management unit may receive, via appropriate network interfaces a health related record per a given User from external sources, such as a physician and/or an authorized diet consultant. It is preferred that User related data records is protected by computer security means, such as encryption, authentication and user authorization, which allows user permission using password or any biometric means, in order to keep User's privacy at the utmost level.

Nutritional Account and Nutritional Credit Card

In addition, the service may provide the User with a Calorie account, which will be handled in a way which is not dissimilar in many aspects from a regular bank account.

For example, the User may be furnished by the service with a Calorie credit card, or in a more general form a nutrition credit card. The card can be provided in various form factors. For example, the card can be embedded in an existing financial credit card, or come in a form of a separate credit card.

As examples of the nutritional credit card usage, the User may perform an order at a restaurant. A database either at the restaurant premises or in another location contains the nutritional data of each dish is maintained as part of the service.

When a User orders a given dish, he may provide the nutritional credit card, and his record at the service provider will be automatically updated. For example, his Calorie update will be updated with the Calorie intake of this dish. As another non-limiting example, if the User suffers from an allergy to Nuts, the system analyzes the dish content vs. the User allergies record and immediately alerts the User or the restaurant stuff for this problem. In particular alerting the User may take place not just after but also before a food intake, to warn the User of e.g., exceeding his intake limitation, allergen or otherwise inappropriate food ingredient specifically for that User, or even for an ingredient, which is not in accordance with the User preferences (e.g., meat for a vegan User, mayonnaise for a User distasting it, etc.). Pertaining to such an example, User preference and allergies information might reside locally on the card or remotely at the service center.

As another non-limited example, the User may use the Nutritional Credit Card at the fitness center, swiping the credit card at a card reader attached to a workout device. The estimated Calorie expenditure information due to the User's workout on the device will be tagged by the User identification and sent to the management unit as a Calorie expenditure record. The management unit can then adjust the Calorie expenditure data according to specific User's information as disclosed in embodiments of the present invention.

Alternatively a proximity sensor can locate the device, which the User is performing the workout upon and attach the workout data to the appropriate User in a semi or full automatic manner.

Nutritional Data Sharing

While nutritional data is private information of the User, and the service provider should provide means to protect the User privacy, some Users may wish to share at least some of their nutritional data. Sharing of nutritional data may be take place with a healthcare provider such as physician and/or diet consultant, with family member, for a close group members of a social network such as Facebook or Google+, or to the general public, again via a social network.

In accordance with the above, an embodiment of the current invention provides the User with means to select the type of nutritional data he/she wishes to share with others.

Figure 21:
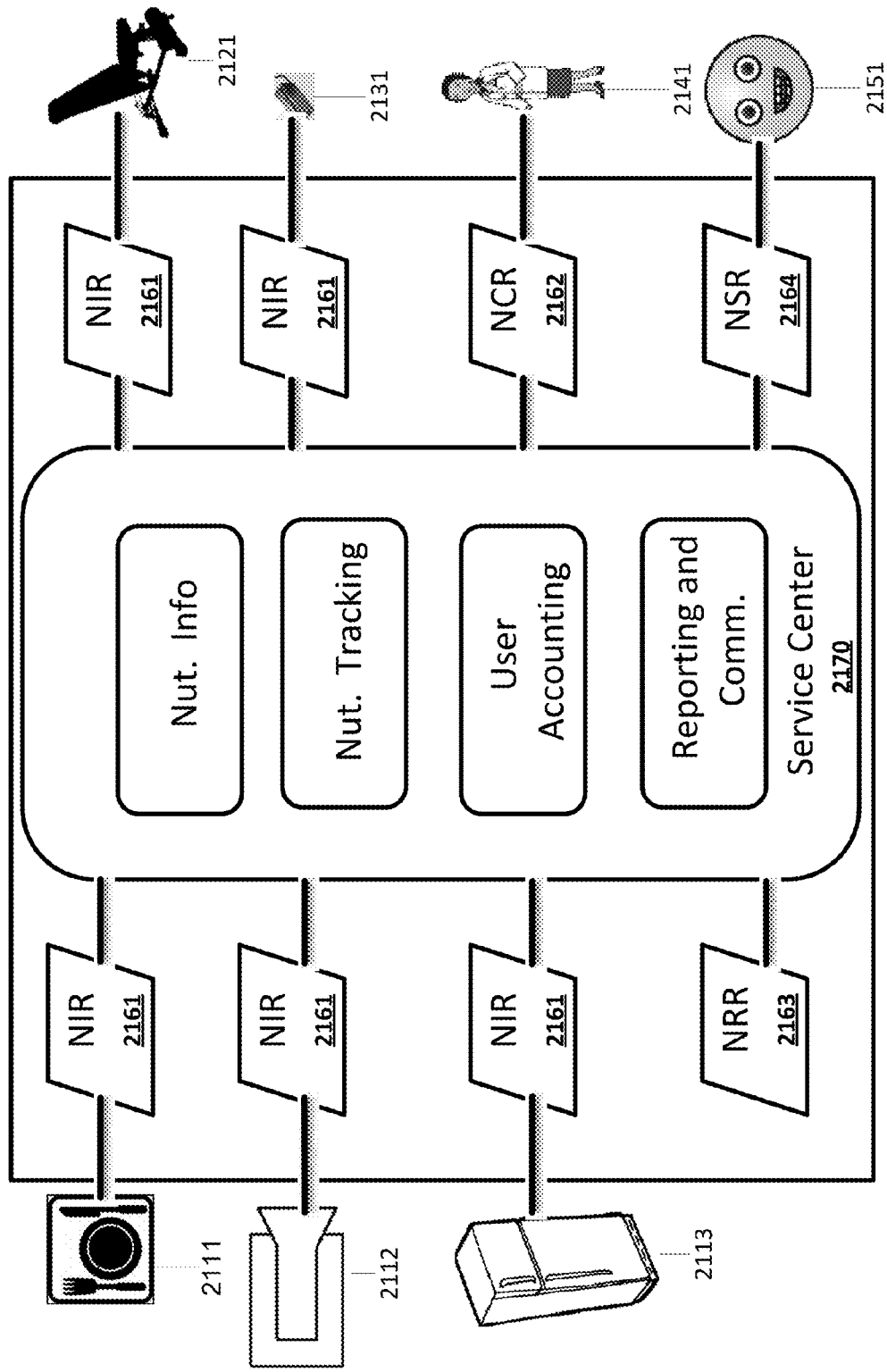
FIG. 21 provides a block diagram of an exemplary embodiment providing a distributed nutrition and calorie balance control, calorie account and data sharing services.

The User is furnished by a User interface, either standalone or as plug-inn to a social network User interface. Via the User interface, the User may select which of his nutritional information items he wishes to share per sharing level. An exemplary set of sharing levels is:

1) User Only—data items exposed to the User only
2) Health Personal—data items exposed also to health personal only
3) Service Provider Stuff—data items exposed also to a service provider stuff
4) Family members—data items exposed also to a family member
5) Group—data items exposed to a given social network group
6) Public—data items exposed to all Users of the social network FIG. 21 depicts a distributed nutrition and Calorie balance, tracking estimation and management service according to exemplary embodiments disclosed herein.

A distributed nutrition and Calorie balance, tracking estimation and management service (2100) may include various nutritional information interfaces, for example, a restaurant (2111) may provide a record of a User Calorie intake and other nutritional information items as described in an exemplary embodiment above. The information might be sent by forming a standardized Nutritional Information Record (NIR—2161), further via a standardized Nutritional Information Protocol (NIP—not shown). The NIR and NIP facilitate an advantaged way of interchanging nutritional information across a computer network, between e.g., devices produced by different vendors in a coherent and secure form. NIR may include for example, User identification details, nutritional information details, time-date information, device identification, locations, and security stamp and confidence levels. NIP may include for example protocol identification codes, record identification codes, security, identification, and encryption layers.

Other examples of interfaces are visual food intake inspection unit (2112), food container (2113) depicted in embodiments of the present invention, as well as a workout device (2121) providing Calorie expenditure information (also depicted in embodiments of the present invention) via a NIR. Interface entities may facilitate the Nutritional Credit card via e.g., a card reader (2131).

A physician and/or an authorized nutrition consultant (2141) may provide to the service general and/or per User's nutritional instruction, providing some constrains on the User Calorie intake, other nutritional constrains, which may further include tolerance values, and possibly desired workout and/or Calorie expenditure figures. Additionally User anatomical and health data may be also provided. This information is sent via a data entity designated as Nutritional Control Record NCR (2162). This information record, which can be formatted as well into a standardized form may further by encapsulated into the Nutritional Information Protocol (NIP).

The reports that are provided by the service over the network, are formatted as a Nutritional Report record (2163), and output or display devices (not shown) for the identified User and/or the appropriate personnel such as the physician and/or nutrition consultant. As with the other described above types of record, NRR can be standardized and encapsulated into the Nutritional Information Protocol (NIP).

Further on, nutritional data sharing over the network, using e.g., social network may materialize as disclosed above in an embodiment of the present invention. A Nutritional Sharing Record (NSR —2164) may include the shared data, with controlled access to the data items according to the above set of levels. As with the other described above types of record, NSR can be standardized and encapsulated into the Nutritional Information Protocol (NIP).

The Service Center (2170), not necessarily residing in a single physical premises, provide the central processing, tracking and accounting capabilities, and is connected either directly or indirectly, via a computer network to various nutritional information interfaces. It may include:

(a) A Nutritional Information Unit, which stores and processes incoming NIR data records from various sources.

(b) A Nutritional Tracking Unit, which tracks the User's Calorie balance, nutritional information and data provided via Nutritional Control Record. The Nutritional Tracking Unit may also provide various types of nutritional control feedback. For example, it may remotely control the operation of interface devices, such as Food Container Locking Control, Workout device control, e.g., remotely increase/decrease the difficulty level of a workout device according to NIR and NSR data from the specific workout device and/or other interfaces. The unit may also remotely control the operation of other devices and it can be done in real time, or in some other periodical sequence. As another such Nutritional control feedback example, the Nutritional Tracking Unit may also provide the User with real-time indications and alert, e.g., showing real-time daily Calorie balance and/or alert in case of some desired nutritional limitation has been breached.

(c) A User Accounting unit—stores and processes e.g., User identification and authorization data, billing records etc.

(d) Reporting and Communication Unit—handles the reports, data sharing and communication functionalities of the centers.

Reports

The system automatically creates daily, weekly and monthly reports to the User. The report shows all Calorie intake and outtake of the User and may be augmented with the User weight. The reports may contain graphs showing the daily intake and outtake of the User in various parameters (Calories, protein/carb ratio, energy outtake, etc.) Those reports may as a non-limiting example calculate the number of grams of Protein consumed by the User per day. Other reports described in previous embodiments will also be produced.

An embodiment is also disclosed comprising an article of manufacture utilized for implementing the above embodiments.

Figure 22:
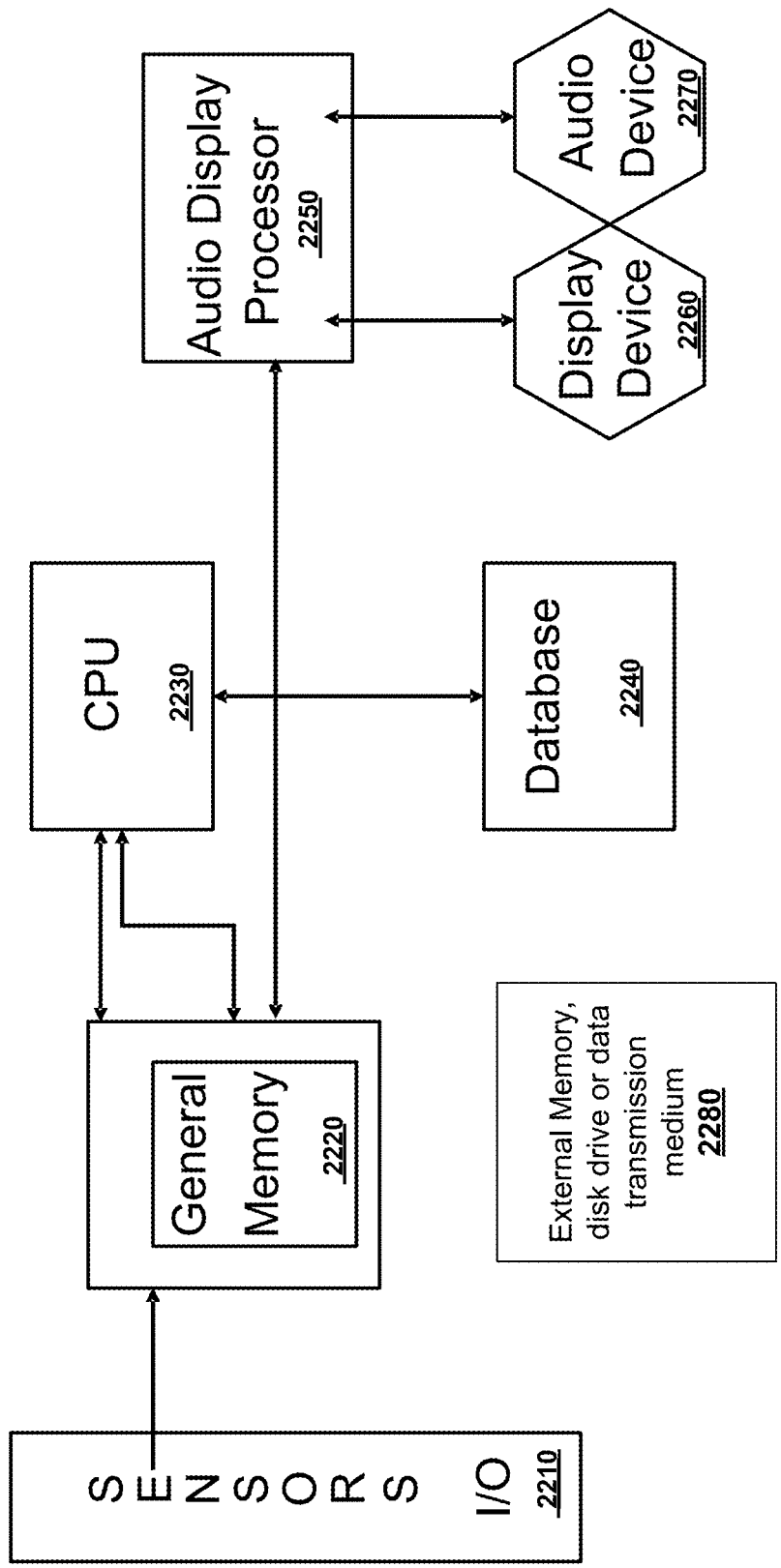
FIG. 22 is a block diagram of exemplary supporting system hardware.

FIG. 22 is a block diagram illustrating the supporting hardware implementation of the various modules in a preferred embodiment. The multiple modules described hereafter operate on a computer system with a central processing unit 2230, input and output (I/O) and sensor devices 2210, volatile and/or nonvolatile memory 2220, a non-volatile Database memory 2240, Display/Audio Processor 2250, Display Output Device 2260, and Audio Output Device 2270. The input and output (I/O) devices may include an Internet connection, a connection to various input and output (I/O) devices, and a connection to various input devices such as a touch screen, a microphone and one or more cameras. The operational logic may be stored as instructions on a computer-readable medium such as an external memory, disk drive or data transmission medium 2280. In addition, part of the memory can be pre-allocated for fast sensor data processing.

It would be understood by a person with an average proficiency in the art that an application may share the display and input device(s) with other concurrently running applications, and therefore, the term Application may relate to a plurality of concurrently running applications.

One skilled in the art will recognize that the particular arrangement and items shown are merely exemplary, and that many other arrangements may be contemplated without departing from the essential characteristics of the present invention. As will be understood by those familiar with the art, the present invention may be embodied either fully or partially in other specific forms without departing from the spirit or essential characteristics thereof. The particular architectures depicted above are merely exemplary of implementations of the present invention. The functional elements and method steps described above are provided as illustrative examples of one technique for implementing the present invention; one skilled in the art will recognize that many other implementations are possible without departing from the present invention as recited in the claims. Likewise, the particular capitalization or naming of the modules, protocols, tokens, attributes, characteristics or any other aspect is not mandatory or significant, and the mechanisms that implement the present invention or its features may have different names or formats. In addition, the present invention may be implemented as a method, a process, a User interface, and a computer program product comprising a computer-readable medium, system, apparatus, or any combination thereof. Accordingly, the disclosure of the present invention is intended to be illustrative, but not limiting, of the scope of the invention, which is set forth in the following claims.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

What is claimed is:

1. A method for non-invasive monitoring food intake comprising:
   at least one means for user identification; at least one means for identification of a food type providing at least one nutritional information item pertaining to the food type;
   at least one means for consumption analysis providing at least one of volume and weight the at least one food type that has been consumed by the user, and
   wherein the at least one means for consumption analysis is at least partially based on counting a number and length of time of bite chewing of food intake by the user and an estimation of a volume of each bite of a food intake by using the user identification and a food type and the length of time of bite chewing.

2. The method for monitoring food intake of claim 1, wherein the at least one user identification includes User authorization.

3. The method for monitoring food intake of claim 1, wherein the at least one food identification method is selectable from at least one plate analysis, hand analysis, bun analysis or a combination thereof.

4. The method for monitoring food intake of claim 1, wherein the at least one food identification method consists of visual comparing of plate portions with a known set of food plates or food items.

5. The method for monitoring food intake of claim 1, wherein the at least one method of counting the number and length of bite chewing uses a visual inspection of a mouth.

6. A method for providing a distributed nutritional and calorie balance control service over a computer data network comprising:
   at least one means for user identification and/or user authorization;
   at least one means for food identification providing at least one nutritional information item pertaining to at least one food type;
   at least one means for consumption analysis, providing information on volume of the at least one food type has been consumed by the user;
   at least one means for estimating calorie expenditure by the user; and
   a management means for gathering user consumption analysis and calorie expenditure records over the computer data network and provide nutritional control feedback to the user.

7. A system that non-invasively monitors food intake comprising:
   at least one means for user identification;
   at least one means for identification of food type providing at least one nutritional information item pertaining to at least one of the food type;
   at least one means for consumption analysis providing at least one of volume and weight of the said at least one food type that has been consumed by the user, and
   wherein the at least one means for consumption analysis is at least partially based on counting a number and length of time of bite chewing of food intake by the user and an estimation of a volume of each bite of a food intake by using the user identification and food type and the length of time of bite chewing.

* * * * *